United States Patent
Chern et al.

(10) Patent No.: US 10,446,696 B2
(45) Date of Patent: *Oct. 15, 2019

(54) BACK-ILLUMINATED SENSOR WITH BORON LAYER

(71) Applicant: KLA-Tencor Corporation, Milpitas, CA (US)

(72) Inventors: Jehn-Huar Chern, Santa Clara, CA (US); Ali R. Ehsani, San Ramon, CA (US); Gildardo Delgado, Livermore, CA (US); David L. Brown, Los Gatos, CA (US); Yung-Ho Alex Chuang, Cupertino, CA (US); John Fielden, Los Altos, CA (US)

(73) Assignee: KLA-Tencor Corporation, Milpitas, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/151,225

(22) Filed: Oct. 3, 2018

(65) Prior Publication Data

US 2019/0131465 A1    May 2, 2019

Related U.S. Application Data

(63) Continuation of application No. 15/797,970, filed on Oct. 30, 2017, now Pat. No. 10,121,914, which is a (Continued)

(51) Int. Cl.
*G01N 21/88* (2006.01)
*G01N 21/95* (2006.01)
(Continued)

(52) U.S. Cl.
CPC ..... *H01L 31/0216* (2013.01); *G01N 21/8806* (2013.01); *G01N 21/9501* (2013.01);
(Continued)

(58) Field of Classification Search
CPC ............. G01N 23/16; G01N 21/8806; H01L 31/0216; H01L 27/14646; H01L 27/1464
See application file for complete search history.

(56) References Cited

U.S. PATENT DOCUMENTS 3,755,704 A   8/1973 Spindt et al.
3,870,917 A   3/1975 Cuny
(Continued)

FOREIGN PATENT DOCUMENTS

EP   0602983 A1   6/1994
EP   0746871 A1   12/1996
(Continued)

OTHER PUBLICATIONS

U.S. Appl. No. 61/720,700-Certified Copy corres to PCT/EP2013/071080, pp. 1-44.
(Continued)

*Primary Examiner* — David P Porta
*Assistant Examiner* — Djura Malevic
(74) *Attorney, Agent, or Firm* — Bever, Hoffman & Harms, LLP

(57) ABSTRACT

An inspection system including an optical system (optics) to direct light from an illumination source to a sample, and to direct light reflected/scattered from the sample to one or more image sensors. At least one image sensor of the system is formed on a semiconductor membrane including an epitaxial layer having opposing surfaces, with circuit elements formed on one surface of the epitaxial layer, and a pure boron layer and a doped layer on the other surface of the epitaxial layer. The image sensor may be fabricated using CCD (charge coupled device) or CMOS (complementary metal oxide semiconductor) technology. The image sensor may be a two-dimensional area sensor, or a one-dimensional array sensor. The image sensor can be included
(Continued)

in an electron-bombarded image sensor and/or in an inspection system.

18 Claims, 15 Drawing Sheets

Related U.S. Application Data continuation of application No. 15/182,200, filed on Jun. 14, 2016, now Pat. No. 9,818,887, which is a continuation of application No. 13/792,166, filed on Mar. 10, 2013, now Pat. No. 9,496,425.

(60) Provisional application No. 61/658,758, filed on Jun. 12, 2012, provisional application No. 61/622,295, filed on Apr. 10, 2012.

(51) Int. Cl.
    *H01L 31/0216*    (2014.01)
    *G01N 21/956*    (2006.01)
    *H01L 27/146*    (2006.01)
    *H01L 27/148*    (2006.01)

(52) U.S. Cl.
    CPC ....... *G01N 21/956* (2013.01); *H01L 27/1462* (2013.01); *H01L 27/1464* (2013.01); *H01L 27/14685* (2013.01); *H01L 27/14806* (2013.01); *G01N 2021/95676* (2013.01); *H01L 27/14689* (2013.01)

(56) References Cited

U.S. PATENT DOCUMENTS

| | | |
|---|---|---|
| 3,947,707 A | 3/1976 | Shannon et al. |
| 4,099,198 A | 7/1978 | Howorth et al. |
| 4,210,922 A | 7/1980 | Shannon |
| 4,275,326 A | 6/1981 | Houtkamp |
| 4,348,690 A | 9/1982 | Jastrzebski et al. |
| 4,467,189 A | 8/1984 | Tsuchiya |
| 4,555,731 A | 11/1985 | Zinchuk |
| 4,644,221 A | 2/1987 | Gutierrez et al. |
| 4,760,031 A | 7/1988 | Janesick |
| 4,853,595 A | 8/1989 | Alfano et al. |
| 5,054,683 A | 10/1991 | Haisma et al. |
| 5,120,949 A | 6/1992 | Tomasetti |
| 5,144,630 A | 9/1992 | Lin |
| 5,227,313 A | 7/1993 | Gluck et al. |
| 5,315,126 A | 5/1994 | Field |
| 5,376,810 A | 12/1994 | Hoenk et al. |
| 5,428,392 A | 6/1995 | Castro et al. |
| 5,563,702 A | 10/1996 | Emery et al. |
| 5,717,518 A | 2/1998 | Shafer et al. |
| 5,719,069 A | 2/1998 | Sparks |
| 5,731,584 A | 3/1998 | Beyne et al. |
| 5,742,626 A | 4/1998 | Mead et al. |
| 5,760,809 A | 6/1998 | Malhotra et al. |
| 5,760,899 A | 6/1998 | Eismann |
| 5,852,322 A | 12/1998 | Speckbacher |
| 5,940,685 A | 8/1999 | Loomis et al. |
| 5,999,310 A | 12/1999 | Shafer et al. |
| 6,013,399 A | 1/2000 | Nguyen |
| 6,064,759 A | 5/2000 | Buckley et al. |
| 6,162,707 A | 12/2000 | Dinh et al. |
| 6,201,257 B1 | 3/2001 | Stettner et al. |
| 6,201,601 B1 | 3/2001 | Vaez-Iravani et al. |
| 6,220,914 B1 | 4/2001 | Lee et al. |
| 6,271,916 B1 | 8/2001 | Marxer et al. |
| 6,278,119 B1 | 8/2001 | Nikzad et al. |
| 6,285,018 B1 | 9/2001 | Aebi et al. |
| 6,297,879 B1 | 10/2001 | Yang et al. |
| 6,307,586 B1 | 10/2001 | Costello |
| 6,346,700 B1 | 2/2002 | Cunningham et al. |
| 6,362,484 B1 | 3/2002 | Beyne et al. |
| 6,373,869 B1 | 4/2002 | Jacob |
| 6,403,963 B1 | 6/2002 | Nikzad et al. |
| 6,535,531 B1 | 3/2003 | Smith et al. |
| 6,545,281 B1 | 4/2003 | McGregor et al. |
| 6,608,676 B1 | 8/2003 | Zhao et al. |
| 6,711,283 B1 | 3/2004 | Soenksen |
| 6,837,766 B2 | 1/2005 | Costello |
| 7,005,637 B2 | 2/2006 | Costello et al. |
| 7,039,157 B2 | 5/2006 | Fujii et al. |
| 7,126,699 B1 | 10/2006 | Wihl et al. |
| 7,130,039 B2 | 10/2006 | Vaez-Iravani et al. |
| 7,136,159 B2 | 11/2006 | Tsai et al. |
| 7,141,791 B2 | 11/2006 | Masnaghetti et al. |
| 7,283,166 B1 | 10/2007 | Billman |
| 7,321,468 B2 | 1/2008 | Herkommer et al. |
| 7,345,825 B2 | 3/2008 | Chuang et al. |
| 7,352,457 B2 | 4/2008 | Kvamme et al. |
| 7,432,517 B2 | 10/2008 | Botma et al. |
| 7,446,474 B2 | 11/2008 | Maldonado et al. |
| 7,465,935 B2 | 12/2008 | Urano et al. |
| 7,525,649 B1 | 4/2009 | Leong et al. |
| 7,528,943 B2 | 5/2009 | Brown et al. |
| 7,586,108 B2 | 9/2009 | Nihtianov et al. |
| 7,609,309 B2 | 10/2009 | Brown et al. |
| 7,714,287 B1 | 5/2010 | James et al. |
| 7,741,666 B2 | 6/2010 | Nozaki et al. |
| 7,750,280 B2 | 7/2010 | Hwang et al. |
| 7,791,170 B2 | 9/2010 | Chiang et al. |
| 7,800,040 B2 | 9/2010 | Blacksberg et al. |
| 7,813,406 B1 | 10/2010 | Nguyen et al. |
| 7,838,833 B1 | 11/2010 | Lent et al. |
| 7,875,948 B2 | 1/2011 | Hynecek et al. |
| 7,928,382 B2 | 4/2011 | Hatakeyama et al. |
| 7,952,633 B2 | 5/2011 | Brown et al. |
| 7,985,658 B2 | 7/2011 | Lei et al. |
| 8,017,427 B2 | 9/2011 | Manabe |
| 8,138,485 B2 | 3/2012 | Nihtianov et al. |
| 8,309,443 B2 | 11/2012 | Tanaka et al. |
| 8,323,406 B2 | 12/2012 | Bondokov et al. |
| 8,450,820 B2 | 5/2013 | Nanver et al. |
| 8,455,971 B2 | 6/2013 | Chen et al. |
| 8,513,587 B2 | 8/2013 | Wang et al. |
| 8,514,587 B2 | 8/2013 | Zhang et al. |
| 8,629,384 B1 | 1/2014 | Biellak et al. |
| 8,686,331 B2 | 4/2014 | Armstrong |
| 8,755,417 B1 | 6/2014 | Dribinski |
| 8,803,075 B2 | 8/2014 | Menge et al. |
| 8,873,596 B2 | 10/2014 | Dribinski et al. |
| 8,891,079 B2 | 11/2014 | Zhao et al. |
| 8,929,406 B2 | 1/2015 | Chuang et al. |
| 9,426,400 B2 | 8/2016 | Brown et al. |
| 9,478,402 B2 | 10/2016 | Chuang et al. |
| 9,496,425 B2 | 11/2016 | Chern et al. |
| 9,529,182 B2 | 12/2016 | Chuang et al. |
| 9,601,299 B2 | 3/2017 | Chuang et al. |
| 9,608,399 B2 | 3/2017 | Chuang et al. |
| 9,748,294 B2 | 8/2017 | Muramatsu et al. |
| 2001/0017344 A1 | 8/2001 | Aebi |
| 2003/0043876 A1 | 3/2003 | Lublin et al. |
| 2003/0222579 A1 | 12/2003 | Habib et al. |
| 2004/0021061 A1 | 2/2004 | Bijkerk |
| 2004/0056279 A1 | 3/2004 | Niigaki et al. |
| 2004/0227070 A1 | 11/2004 | Bateman et al. |
| 2005/0122021 A1 | 6/2005 | Smith et al. |
| 2005/0167575 A1 | 8/2005 | Benz et al. |
| 2005/0190452 A1 | 9/2005 | Govorkov et al. |
| 2005/0196059 A1 | 9/2005 | Inoue et al. |
| 2005/0233493 A1 | 10/2005 | Augusto et al. |
| 2005/0264148 A1 | 12/2005 | Maldonado et al. |
| 2006/0054778 A1 | 3/2006 | Suhling |
| 2006/0055321 A1 | 3/2006 | Maldonado et al. |
| 2006/0069460 A1 | 3/2006 | Smith et al. |
| 2006/0170324 A1 | 8/2006 | Machuca et al. |
| 2006/0188869 A1 | 8/2006 | Zeskind et al. |
| 2007/0002465 A1 | 1/2007 | Chuang et al. |
| 2007/0034987 A1 | 2/2007 | Costello et al. |
| 2007/0064135 A1 | 3/2007 | Brown et al. |
| 2007/0096648 A1 | 5/2007 | Nakajima et al. |
| 2007/0103769 A1 | 5/2007 | Kuwabara |

(56) References Cited

U.S. PATENT DOCUMENTS

| | | |
|---|---|---|
| 2007/0188744 A1 | 8/2007 | Leslie et al. |
| 2007/0291810 A1 | 12/2007 | Luo et al. |
| 2008/0044932 A1 | 2/2008 | Samoilov et al. |
| 2008/0173903 A1 | 7/2008 | Imai et al. |
| 2008/0315092 A1 | 12/2008 | Kley |
| 2008/0315121 A1 | 12/2008 | Nihtianov et al. |
| 2009/0021717 A1 | 1/2009 | Nihtianov et al. |
| 2009/0045325 A1 | 2/2009 | Tomuta et al. |
| 2009/0091752 A1 | 4/2009 | Terasawa et al. |
| 2009/0108207 A1 | 4/2009 | Liu |
| 2009/0125242 A1 | 5/2009 | Choi et al. |
| 2009/0128912 A1 | 5/2009 | Okada et al. |
| 2009/0168152 A1 | 7/2009 | Gelernt et al. |
| 2009/0180176 A1 | 7/2009 | Armstrong et al. |
| 2009/0324234 A1 | 12/2009 | Kashima |
| 2010/0102213 A1 | 4/2010 | Garris |
| 2010/0103409 A1 | 4/2010 | Ohshima et al. |
| 2010/0148667 A1 | 6/2010 | Niigaki et al. |
| 2010/0188655 A1 | 7/2010 | Brown et al. |
| 2010/0208979 A1 | 8/2010 | Abbott et al. |
| 2010/0233869 A1 | 9/2010 | Park et al. |
| 2011/0073982 A1 | 3/2011 | Armstrong et al. |
| 2011/0101219 A1 | 5/2011 | Uchiyama et al. |
| 2011/0116077 A1 | 5/2011 | Chuang et al. |
| 2011/0168886 A1 | 7/2011 | Shadman et al. |
| 2011/0169116 A1 | 7/2011 | Nanver et al. |
| 2011/0234790 A1 | 9/2011 | True |
| 2011/0256655 A1 | 10/2011 | Nikzad et al. |
| 2011/0261354 A1 | 10/2011 | Sinfield et al. |
| 2011/0291109 A1 | 12/2011 | Wraback et al. |
| 2012/0007920 A1 | 1/2012 | Takahashi |
| 2012/0012811 A1 | 1/2012 | Deflumere et al. |
| 2012/0012957 A1 | 1/2012 | Larsen et al. |
| 2012/0081684 A1 | 4/2012 | Den et al. |
| 2012/0132823 A1 | 5/2012 | Menge et al. |
| 2012/0160993 A1 | 6/2012 | Nevet et al. |
| 2012/0170021 A1 | 7/2012 | Walsh |
| 2012/0217558 A1 | 8/2012 | Togashi |
| 2012/0228485 A1 | 9/2012 | Iwakiri et al. |
| 2012/0268722 A1 | 10/2012 | Nihtianov et al. |
| 2013/0009069 A1 | 1/2013 | Okada |
| 2013/0016346 A1 | 1/2013 | Romanovsky et al. |
| 2013/0017205 A1 | 1/2013 | Giaccia et al. |
| 2013/0020491 A1 | 1/2013 | Mazzillo |
| 2013/0056843 A1 | 3/2013 | Lee et al. |
| 2013/0077086 A1 | 3/2013 | Chuang et al. |
| 2013/0082241 A1 | 4/2013 | Kub et al. |
| 2013/0088706 A1 | 4/2013 | Chuang et al. |
| 2013/0126705 A1 | 5/2013 | Maleev |
| 2013/0148112 A1 | 6/2013 | Chuang et al. |
| 2013/0169957 A1 | 7/2013 | Wolf et al. |
| 2013/0176552 A1 | 7/2013 | Brown et al. |
| 2013/0270663 A1 | 10/2013 | Lin et al. |
| 2013/0313440 A1 | 11/2013 | Chuang et al. |
| 2013/0320211 A1 | 12/2013 | Park et al. |
| 2013/0336574 A1 | 12/2013 | Nasser-Ghodsi et al. |
| 2013/0341504 A1 | 12/2013 | Neill et al. |
| 2014/0151552 A1 | 6/2014 | Jiang et al. |
| 2014/0203386 A1 | 7/2014 | Bui et al. |
| 2014/0246595 A1 | 9/2014 | Menge et al. |
| 2014/0305367 A1 | 10/2014 | Chuang et al. |
| 2014/0362203 A1 | 12/2014 | Delaney et al. |
| 2015/0007765 A1 | 1/2015 | Dribinski |
| 2015/0294998 A1 | 10/2015 | Nihtianov et al. |

FOREIGN PATENT DOCUMENTS

| | | |
|---|---|---|
| EP | 1939917 A2 | 7/2008 |
| EP | 2346094 A1 | 7/2011 |
| JP | H08241977 A | 9/1996 |
| JP | H10171965 A | 6/1998 |
| JP | 2002033473 | 1/2002 |
| JP | 2004031452 A | 1/2004 |
| JP | 2007040909 A | 2/2007 |
| JP | 2007086108 A | 4/2007 |
| JP | 2009117454 A | 5/2009 |
| JP | 2010003755 A | 1/2010 |
| KR | 100688497 B1 | 3/2007 |
| KR | 100826407 B1 | 5/2008 |
| RU | 2297070 C2 | 4/2007 |
| WO | 9532518 A1 | 11/1995 |
| WO | 9617372 A1 | 6/1996 |
| WO | 2007035858 A2 | 3/2007 |
| WO | 2011091159 A1 | 7/2011 |
| WO | 2013006867 A1 | 1/2013 |
| WO | 2014067754 A2 | 5/2014 |

OTHER PUBLICATIONS

Allen et al., Work Function, Photoelectric Threshold, and Surface . . . ; Physical Review, vol. 127, No. 1, Jul. 1, 1962, pp. 150-158.

Armstrong, Carter M.The Quest for the Ultimate Vacuum Tube, Spectrum IEEE, Dec. 2015, 4 pgs.

Ding, MengField Emission from Silicon, MIT 2001, 277 pgs.

Fanton et al, Multiparameter Measurements of Thin Film . . . , Journal of Applied Physics, vol. 73, No. 11, p. 7035 (1993).

Field Emitter Review, 7 pgs in Japanese.

Fowler, R. H., et al, Electron Emission in Intense Electric Fields, Mar. 31, 1928, 9 pgs.

Fu et al., Optimizing GaN photocathode structure for higher . . . ; Optik, vol. 123, No. 9, May 2012, pp. 756-768.

Hecht, Optics, Fourth Edition, India: Pearson Education Pte, Ltd. 2004.

Hecht, Optics, Second Edition, Adelphi University, 1987, Addison-Wesley Publishing Company, Inc., 3 pages.

Henderson, Brian S., Study of Negative Electron Affinity . . . , Dept. of Physics, Rice Univ., Aug. 7, 2009, 18 pgs.

Howorth et al., Transmission silicon photoemitters . . . , Jml of Physics D: Applied Physics, vol. 9, No. 5, Apr. 1, 1976, pp. 785-794.

ISR and Written Opinion dated Mar. 31, 2014 for PCT/US2013/074124.

Janesick, James R., Scientific Charge-Coupled Devices, SPIE Press, 2001, pp. 556-561.

KLA-Tencor Coporation, filed U.S. Appl. No. 62/059,368, filed Oct. 3, 2014 and entitled "183nm Laser and Inspection System".

Koike, AkifumiField Emitter Equipped With a Suppressor to Control Emission Angel, IEEE Electron Device Letters, vol. 34, No. 5, May 2013, 3 pgs.

Martinelli, Ramon U., Infrared Photoemission from Silicon, Applied Physics Letters, vol. 16, No. 7, Apr. 1, 1970, pp. 261-262.

Martinelli, Ramon U., Reflection and Transmission Secondary Emission . . . , Applied Physics Letters, vol. 17, No. 8, Oct. 15, 1970, pp. 313-314.

Nagao, Masayoshi, Cathode Technologies for Field Emission Displays, IEEJ Trans 2006; 1:171-178, 8 pgs.

Nagao, MasayoshiFabrication of a Field Emitter Array with a Built-In Einzel Lens, JJAP 48 (2008) 06FK02, 4 pgs.

Nanver et al., Pure-Boron Chemical-Vapor-Deposited Layers: a New Material for Silicon Device Processing, 18th IEEE International Conference on Advanced Thermal Processing of Semiconductors (RTP), Sep. 28, 2010-Oct. 1, 2010, pp. 136-139.

Nanver, Silicon Photodiodes for Low Penetration Depth Beams such as DUV/VUV/EUV Light and Low-Energy Electrons, Advances in Photodiodes, G. Betta, ed., Mar. 22, 2011, pp. 205-224, www.intechopen.com.

Neo, YoichiroElectron Optical Properties of Microcolumn with Field Emitter, JJAP 52 (2013) 036603, 5 pgs.

Pain; et al., "Pain et al., "A Back-Illuminated Megapixel CMOS Image Sensor", Jun. 9, 2005, IEEE Workshop on Charge-Coupled Devices and Advanced Image Sensors, Karuizawa, Japan, 4 pgs.".

Rakhshandehroo, M.R. et al, Fabrication of a self-aligned silicon field emission . . . , JVSTB, 16, 765 (1998); doi: 10.1116/1,589900, 6 pgs.

Rakhshandehroo, M.R. et al, Field emission from gated Si emitter tips with precise . . . , JVSTB, 15, 2777 (1997); doi: 10.1116/1.589726, 6 pgs.

Raoult, Efficient generation of narrow-bandwidth . . . , Jul. 15, 1998, vol. 23, No. 14, Optics Letters, pp. 1117-1119.

(56) References Cited

OTHER PUBLICATIONS

Sarubbi et al., Chemical Vapor Deposition of α-Boron Layers on Silicon for Controlled Nanometer-Deep p+ n Junction Formation, J. Electron. Mat, vol. 39, No. 2, Feb. 2010, pp. 162-173.
Sarubbi et al., Pure boron-doped photodiodes . . . IEEE, Sep. 15, 2008, pp. 278-281.
Sato, T. et al, Fabrication and characterization of HfC coated . . . , J. Vac. Sci. Technol. B 2194), published Jul. 31, 2003, 5 pgs.
Serbun Pavel et al, Stable field emission of single B-doped . . . , JVSTB, 31, 02B101 (2013); doi: 10.1116/1.4765088, 7 pgs.
Sobieski, Stanley, Intensified Charge Coupled Devices For Ultra Low Light Level Imaging, NASA, Goddard Space Flight Center, SPIE vol. 78 (1976) Low Light Level Devices, pp. 73-77.
Tobin, Kenneth W., Inspection in Semiconductor Manufacturing, Webster's Encyclopedia of Electrical and Electronic Engineering, vol. 10, pp. 242-262, Wiley & Sons, NY, NY, 1999.
Utsumi, TakaoVacuum Microelectrnoics: What's New and Exciting, IEEE vol. 38, No. 10, Oct. 1991, 8 pgs.
Xiaogian, Fu, Higher Quantum Efficiency by Optimizing . . . 978-1-4244-6644-3/10 IEEE, pp. 234-235.

100

```
┌─────────────────────────────────────────────────────┐
│ Create front-side circuit elements without any metal │
│ interconnects 101                                   │
└─────────────────────────────────────────────────────┘
                         ↓
┌─────────────────────────────────────────────────────┐
│ Back-thin active sensor area                        │
│ 103                                                 │
└─────────────────────────────────────────────────────┘
                         ↓
┌─────────────────────────────────────────────────────┐
│ Deposit protective layer over front-side surface    │
│ 105                                                 │
└─────────────────────────────────────────────────────┘
                         ↓
┌─────────────────────────────────────────────────────┐
│ Clean and prepare back-side surface for boron deposition │
│ 107                                                 │
└─────────────────────────────────────────────────────┘
                         ↓
┌─────────────────────────────────────────────────────┐
│ Perform high-temperature surface treatment          │
│ 109                                                 │
└─────────────────────────────────────────────────────┘
                         ↓
┌─────────────────────────────────────────────────────┐
│ Deposit pure boron layer on back-side surface       │
│ 111                                                 │
└─────────────────────────────────────────────────────┘
                         ↓
┌─────────────────────────────────────────────────────┐
│ Remove or pattern protective layer                  │
│ 113                                                 │
└─────────────────────────────────────────────────────┘
                         ↓
┌─────────────────────────────────────────────────────┐
│ Fabricate interconnects on front-side surface       │
│ 115                                                 │
└─────────────────────────────────────────────────────┘
                         ↓
┌─────────────────────────────────────────────────────┐
│ Package device                                      │
│ 117                                                 │
└─────────────────────────────────────────────────────┘
```

Figure 1

BACK-ILLUMINATED SENSOR WITH BORON LAYER

RELATED APPLICATIONS

The present application is a continuation of U.S. patent application Ser. No. 15/797,970, entitled "BACK-ILLUMINATED SENSOR WITH BORON LAYER" by Chern et al. and filed on Oct. 30, 2017, which is a continuation of U.S. Pat. No. 9,818,887, entitled "BACK-ILLUMINATED SENSOR WITH BORON LAYER" by Chern et al. and issued on Nov. 14, 2017, which is a continuation of U.S. Pat. No. 9,496,425, entitled "BACK-ILLUMINATED SENSOR WITH BORON LAYER" by Chern et al. and issued on Nov. 15, 2016, which claims priority to U.S. Provisional Application 61/658,758, entitled "ELECTRON-BOMBARDED CCD AND INSPECTION SYSTEMS USING ELECTRON-BOMBARDED CCD DETECTORS" by Chuang et al. and filed on Jun. 12, 2012 and to U.S. Provisional Application 61/622,295, entitled "BACK-ILLUMINATED CCD WITH PURE-BORON COATING FOR EUV AND VUV APPLICATION IN MASK AND WAFER INSPECTION" by Chern et al. and filed on Apr. 10, 2012, all of which are incorporated by reference herein.

The present application is also related to U.S. patent application Ser. No. 13/710,315, entitled "ELECTRON-BOMBARDED CHARGE-COUPLED DEVICE AND INSPECTION SYSTEMS USING EBCCD DETECTORS", filed by Chuang et al. on Dec. 10, 2012, which claims priority to U.S. Provisional Application 61/569,611, entitled "ELECTRON-BOMBARDED CHARGE-COUPLED DEVICE AND INSPECTION SYSTEMS USING EBCCD DETECTORS", filed by Chuang et al. on Dec. 12, 2011. The present application is also related to U.S. Provisional Application 61/735,427, entitled "METHOD AND APPARATUS FOR HIGH SPEED ACQUISITION OF MOVING IMAGES USING PULSED ILLUMINATION", filed by Brown et al. on Dec. 10, 2012. All these applications are incorporated by reference herein.

BACKGROUND OF THE DISCLOSURE

Field of the Disclosure

The present application relates to image sensors suitable for sensing radiation in deep UV (DUV), vacuum UV (VUV), and extreme UV (EUV) wavelength, and to methods for making such image sensors. Some embodiments of the sensors are suitable for sensing electrons and other charged particles. All of the sensors are suitable for use in photomask, reticle, or wafer inspection systems.

Related Art

The integrated circuit industry requires inspection tools with increasingly higher resolution to resolve ever smaller features of integrated circuits, photomasks, reticles, solar cells, charge coupled devices etc., as well as detect defects whose sizes are of the order of, or smaller than, those feature sizes.

Inspection systems operating at short wavelengths, e.g. wavelengths shorter than about 250 nm, can provide such resolution in many cases. In other cases, electrons or other charged particles, such as helium (He) nuclei (i.e. alpha particles) may be used. Specifically, for photomask or reticle inspection, it is desirable to inspect using a wavelength identical, or close, to the wavelength that will be used for lithography, i.e. close to 193.4 nm for current generation lithography and close to 13.5 nm for future EUV lithography, as the phase-shifts of the inspection light caused by the patterns will identical or very similar to those caused during lithography. For inspecting semiconductor patterned wafers, inspection systems operating over a relatively broad range of wavelengths, such as a wavelength range that includes wavelengths in the near UV, DUV, and/or VUV ranges, can be advantageous because a broad range of wavelengths can reduce the sensitivity to small changes in layer thicknesses or pattern dimensions that can cause large changes in reflectivity at an individual wavelength.

In order to detect small defects or particles on photomasks, reticles, and semiconductor wafers, high signal-to-noise ratios are required. High photon or particle flux densities are required to ensure high signal-to-noise ratios when inspecting at high speed because statistical fluctuations in the numbers of photons detected (Poisson noise) is a fundamental limit on the signal-to-noise ratio. In many cases, approximately 100,000 or more photons per pixel are needed. Because inspection systems are typically in use 24 hours per day with only short stoppages, the detectors are exposed to large doses of radiation after only a few months of operation.

A photon with a vacuum wavelength of 250 nm has energy of approximately 5 eV. The bandgap of silicon dioxide is about 10 eV. Although it would appear that such wavelength photons cannot be absorbed by silicon dioxide, silicon dioxide as grown on a silicon surface must have some dangling bonds at the interface with the silicon because the silicon dioxide structure cannot perfectly match that of the silicon crystal. Furthermore, because the single dioxide is amorphous, there are likely also some dangling bonds within the material. In practice, there will be a non-negligible density of defects and impurities within the oxide, as well as at the interface to underlying semiconductor, that can absorb photons with deep UV wavelengths, particularly those shorter than about 250 nm in wavelength. Furthermore, under high radiation flux density, two high-energy photons may arrive near the same location within a very short time interval (nanoseconds or picoseconds), which can lead to electrons being excited to the conduction band of the silicon dioxide by two absorption events in rapid succession or by two-photon absorption. EUV photons have very high energies (13.5 nm in wavelength corresponds to photon energy close to 92 eV) and are capable of breaking silicon-oxygen bonds as well as strongly interacting with defects and contaminants in the oxide. Electron and charged-particle detectors typically have to detect electrons or charged particles with energies of a few hundred eV or higher. Energies greater than 10 eV can readily break silicon-oxygen bonds.

As indicated above, high-energy photons and particles can break bonds and ionize atoms in a silicon dioxide layer. Because silicon dioxide is a good insulator, free electrons created in the silicon dioxide may have lifetimes of ms or longer before recombining. Some of these electrons may migrate into the semiconductor material. These electrons create electric fields within the silicon dioxide and between the silicon dioxide and semiconductor. These electric fields can cause electrons created in the semiconductor by absorption of photons to migrate to the surface of the semiconductor and recombine, thereby resulting in lost signal and reduced detector quantum efficiency. Near continuous use of the instrument means that there may be little, or no, time for recovery of the detector, as new free charges are created as fast as, or faster than, they can recombine.

High-energy particles and photons can also cause irreversible changes to the silicon dioxide. Such changes can include reconfiguration of the bonding of atoms or migration of small atoms within the silicon dioxide. At normal operating temperatures of the detector, which are typically in a range from around room temperature to about 50° C., these changes will not recover. In particular, it is known that conventional silicon photodiodes used as EUV detectors degrade in efficiency with use.

The silicon dioxide layer on the surface of semiconductor detectors significantly reduces the efficiency of those detectors for low-energy (less than about 2 kV) electrons. Some low-energy electrons are absorbed by the silicon dioxide, thereby causing the silicon dioxide to charge up and deflect subsequent arriving electrons. Because a native oxide will always form on an exposed silicon surface, silicon detectors necessarily must have some oxide on their surface. Growing or depositing an alternative dielectric material (instead of the oxide) on the surface of the semiconductor results in a much higher density of defect states at the semiconductor to silicon dioxide interface. These defects reduce the quantum efficiency of the detector, especially for photons or charged particles absorbed close to the surface of the semiconductor.

An additional cause of degradation of EUV sensors is that, in a EUV system, a thin layer of carbon builds up over time on any surface exposed to EUV radiation, including the surface of the image sensors and optical elements. This carbon layer, as it becomes thicker, absorbs EUV radiation and reduces the sensitivity of the sensor, as well as reducing the reflectivity of optical elements in the light path. In a EUV system, all surfaces exposed to EUV are periodically cleaned to remove the carbon. This cleaning is usually performed with activated hydrogen (a mixture of atomic hydrogen and hydrogen radicals), which is very effective at removing carbon. However hydrogen radicals affect the oxide on the surface of silicon detectors and can also cause degradation of the performance of those sensors.

Diode detectors suitable for detecting EUV and/or electrons are known in the art. Exemplary diode detectors are described in U.S. Pat. No. 8,138,485, issued to Nihtianov on Mar. 20, 2012, U.S. Pat. No. 7,586,108, issued to Nihtianov on Sep. 8, 2009, U.S. Published Application 2012/0268722 published on Oct. 25, 2012 (filed by Nihtianov), and U.S. Published Application 2011/0169116 published on Jul. 14, 2011 (filed by Nanver). These diode detectors include a thin (1 nm to 20 nm) layer of boron directly on the silicon surface. U.S. Published Application 2011/0169116 further describes an open mesh of a metallic conductor on the surface of such a detector.

These prior-art detectors have contacts formed on the top (light or electron-incident) surface. A disadvantage of having contacts and conductors formed on the illuminated surface is that it is not possible to create a detector with a large number (thousands or millions) of detector elements (pixels) while maintaining high detector efficiency. Each detector element requires multiple control signals, which are typically shared with other detector elements. For full-well capacities of 100,000 electrons or more, detector element dimensions may typically be in the range of about 10 µm to 20 µm. It is not possible to make hundreds or thousands of interconnects that connect these control signals to one another and to drive circuits without covering a substantial fraction of the area of the surface. Because DUV, VUV, and EUV photons and low-energy particles will not penetrate through layers of conductors such as metals and poly-silicon, the area covered by these conductors will have low, or no, sensitivity.

Therefore, a need arises for an image sensor capable of detecting high-energy photons or charged particles yet overcoming the above disadvantages.

SUMMARY OF THE DISCLOSURE

Methods of fabricating image sensors with high-quantum-efficiency for imaging DUV, VUV, and/or EUV radiation and/or charged particles are described. Image sensors fabricated according to these methods are capable of long-life operation under high fluxes of DUV, VUV, EUV, and/or charged particles. These methods include process steps to form light sensitive active and/or passive circuit elements in a layer on a semiconductor (preferably silicon) wafer.

An exemplary method of fabricating an image sensor includes forming an epitaxial layer on a substrate, forming a gate layer on the epitaxial layer, the gate layer comprising one or more layers of dielectric materials such as silicon dioxide and silicon nitride, forming circuit elements on the gate layer comprising poly-silicon and dielectric materials, but no metal films or metal interconnects, thinning the substrate to generate a thinned substrate (also referred to herein as a membrane) and expose at least portions of the epitaxial layer, and forming a pure boron layer directly on the exposed portions of the epitaxial layer. As used herein, the phrase "circuit elements" refers to light sensitive devices such as charge-coupled devices and photodiodes, other semiconductor devices such as transistors, diodes, resistors and capacitors, and electrical interconnections (often called interconnects) between them. In this first exemplary embodiment, the circuit elements formed prior to boron deposition do not include any metal interconnects. These circuit elements are formed using standard semiconductor manufacturing processes including, but not limited to, photolithography, deposition, etching, ion implantation and annealing. Thinning the sample (e.g. a wafer) can be performed using chemical etching and/or polishing. Notably, this thinning can increase the sensitivity of the image sensor to light impinging the back surface. An anti-reflection coating or a conductive coating can be formed on the boron layer. This anti-reflection or conductive coating may increase the transmission of wavelengths of interest into the image sensor and/or protect the image sensor. In one embodiment, at least one exposed portion of the epitaxial layer can be doped after thinning the substrate and before forming the boron layer. After the boron layer has been deposited on the back surface, the circuits on the front surface can be completed, including forming metal interconnects.

Another method of fabricating an image sensor includes forming an epitaxial layer on a substrate, then forming circuit elements on the epitaxial layer. This step may include forming metal interconnects. Either a handling wafer or a protective layer can be formed on the circuit elements. The substrate is then thinned to expose, at least part of, the epitaxial layer. As indicated above, this thinning can increase the sensitivity of the image sensor to light impinging on the back surface. A pure boron layer is formed on the surface of the epitaxial layer exposed in the thinning process. An anti-reflection coating or a conductive coating can be formed on the boron layer. This anti-reflection or conductive coating may increase the transmission of wavelengths of interest into the image sensor and/or protect the image sensor.

Image sensors with high-quantum-efficiency and long-life operation for DUV, VUV, and/or EUV radiation and/or charged particles are described. These image sensors are thinned from the back-side so that they are highly sensitive to radiation or charged particles impinging on the back-side of the image sensors (wherein these image sensors are back-illuminated). Deposited directly on the back surface of the epitaxial layer is a thin (e.g. between about 2 nm and about 20 nm thick) layer high-purity amorphous boron. In some embodiments, an additional layer of material may be coated on the boron. The thickness and material of each layer may be chosen to increase the transmission of wavelength of interest into the image sensor and/or to protect the image sensor.

The image sensors described herein may be fabricated using CCD (charge coupled device) or CMOS (complementary metal oxide semiconductor) technology. The image sensors may be two-dimensional area sensors, or one dimensional array sensors.

An electron-bombarded image sensor is described herein. The electron-bombarded image sensor includes a photocathode that emits electrons when it absorbs a photon or charged particle. Emitted electrons are accelerated towards a solid-state image sensor, such as a CCD image sensor or a CMOS image sensor. The image sensor includes a pure boron layer deposited directly on a thinned substrate, as described above, thereby ensuring that almost all the electrons striking it penetrate into the device. This high level of penetration enables the electron-bombarded image sensor to use a low accelerating voltage (such as an accelerating voltage that is less than 2 kV, or less than 1 kV), thereby resulting in better image resolution and longer sensor lifetime.

A system for inspecting a sample is also described. This system includes an illumination source and two illumination relays for illuminating the sample. Image relay optics are configured to direct light outputs, i.e. reflections and/or transmissions, of the sample to a first channel image mode relay when the light outputs correspond to the first channel illumination relay, and to a second channel image mode relay when the light outputs correspond to the second channel illumination relay. A sensor is configured to receive relay outputs of the first channel image mode relay and the second channel image mode relay. The sensor includes a semiconductor membrane, in which circuit elements are formed on one surface of the membrane and a boron layer is deposited on the opposite surface of the membrane. In this configuration, the sensor is capable of simultaneously detecting two images of the same sample.

An exemplary inspection system is also described. This inspection system includes an illumination source, optics, and a detector. The optics are configured to direct and focus radiation from the illumination source onto a sample. The detector is configured to receive reflected or scattered light from the sample, wherein the optics are further configured to collect, direct, and focus the reflected or scattered light onto the detector. The detector can include one or more image sensors. At least one image sensor includes a semiconductor membrane, wherein the semiconductor membrane includes circuit elements formed on one surface of the semiconductor membrane and a boron layer is deposited on the opposite surface of the semiconductor membrane.

BRIEF DESCRIPTION OF THE DRAWINGS

FIG. 1 illustrates an exemplary method of fabricating an image sensor.

DETAILED DESCRIPTION OF THE DRAWINGS

Figure 2:
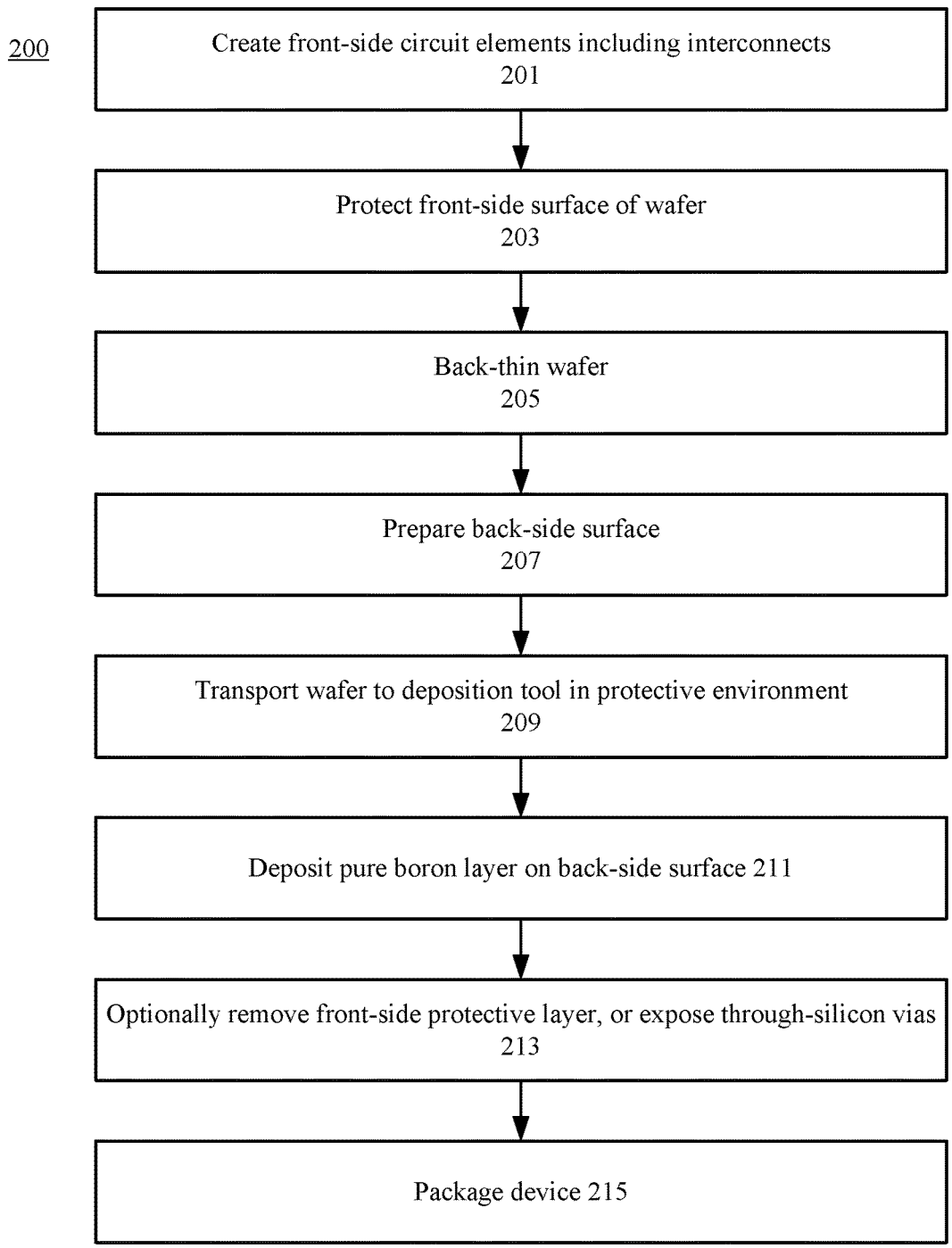
FIG. 2 illustrates an alternative exemplary technique 120 for fabricating an image sensor.

FIG. 1 illustrates an exemplary technique 100 for fabricating an image sensor. In step 101, circuit elements can be created using standard semiconductor processing steps, such as lithography, deposition, ion implantation, annealing, and etching. CCD and/or CMOS sensor elements and devices may also be created during step 101. These circuit elements are created in an epitaxial layer on the front surface of the wafer and therefore are also called front-side circuit elements. In preferred embodiments, the epitaxial (epi) layer is about 20 μm to 40 μm thick. In preferred embodiments, both the epi layer and the substrate are doped with p-type dopants (such as boron), but the epi layer has a much lower dopant concentration (referred to below and in the figures as p−doping) than the bulk wafer (referred to below and in the figures as p+ doping). Typically the epitaxial layer resistivity will be about 10 to 100 Ωcm, and the substrate resistivity will be less than about 0.01 Ωcm. Although poly-silicon interconnects may be formed in step 101, metal interconnects are generally not because metals will be damaged in subsequent high-temperature processing steps.

In step 103, the active sensor areas or even the whole wafer may be thinned from the backside. This thinning typically includes a combination of polishing and etching to expose the epi layer. In one embodiment, the wafer is polished from the backside until the wafer is about 200 μm to 300 μm thick. Then, the front surface and the frame areas around the active sensor areas are protected with a material, such as photoresist or other suitable material. At this point, a chemical etchant is used to etch away the bulk wafer over the active sensor area, thereby exposing the active sensor area. Because the bulk wafer has a much higher dopant concentration and defect density than the epi layer, the etch rate of the bulk semiconductor material is much higher than that of the epi layer. The etch process slows down when it reaches the epi layer, thereby resulting in a uniform thickness membrane area. In another embodiment, the image sensor wafer is bonded to a handle wafer, which might be made of quartz, silicon, sapphire or other material. Then, a polishing process is used to polish the whole wafer until only the epi layer remains.

In step 105, a protective layer can be deposited on the front-side surface to protect the front-side circuit elements during steps 107-111. In particular, any exposed silicon or poly-silicon on the front-side surface must be protected as boron tends to preferentially deposit on silicon. In some embodiments, step 105 may be performed prior to step 103 so that the protective layer can provide additional protection for the front-side surface during the back-thinning process (step 103). In some embodiments, the protective layer may comprise a silicon nitride layer deposited, e.g., using plasma-enhanced CVD deposition.

In step 107, the back-side surface can be cleaned and prepared for boron deposition. During this cleaning, native oxide and any contaminants, including organics and metals, should be removed from the back-side surface. In one preferred embodiment, the cleaning can be performed using a dilute HF solution or an RCA clean process (which is a well-known set of wafer cleaning steps including the removal of organic contaminants, the thin oxide layer, and ionic contamination). After cleaning and during preparation, the wafer is preferably dried using the Marangoni drying technique (surface tension based drying technology) or a similar technique to leave the surface dry and free of water marks. In preferred embodiments, the wafer is protected in a controlled atmosphere during steps 107-109 (using, e.g. dry nitrogen) to minimize native oxide regrowth.

In step 109, the wafer can be held at a high-temperature for a few minutes in a reducing environment, such as a dilute hydrogen gas or a low-pressure hydrogen gas. In preferred embodiments, the wafer can be held at a temperature of approximately 800° C. for about 4 minutes. This high temperature can remove any native oxide layer that might have regrown following step 107.

In step 111, an amorphous layer of pure boron is deposited on the back-side of the back-side surface. In one preferred embodiment, this deposition can be performed using a mixture of diborane and hydrogen gases at a temperature of about 700-800° C. to create a high-purity amorphous boron layer. The thickness of the boron layer depends on the intended application for the sensor. Typically, the boron layer thickness is between about 2 nm and 20 nm. The minimum thinness is generally limited by the need for a pinhole-free uniform film. The maximum thickness generally depends on the absorption of the photons or charged particles of interest by the boron. Note that steps 109 and 111 can be performed in the same process tool and, preferably, in the same process chamber, thereby ensuring that steps 109 and 111 can be performed in quick succession with no possibility of surface contamination or oxide growth between the steps. More details on boron deposition can be found in "Chemical vapor deposition of a-boron layers on silicon for controlled nanometer-deep $p^+$-n junction formation," Sarubbi et al., J. Electron. Material, vol. 39, pp. 162-173, 2010.

The purity and lack of pinholes in the boron layer are critical to the sensitivity and lifetime of the image sensors disclosed herein. If any native oxide film is not removed from the epi layer surface before deposition of the boron, then that native oxide will be affected by DUV, VUV and EUV photons and by charged particles and will cause a degradation of sensor performance with use. Even if all the native oxide is removed prior to the boron deposition, if there are pinholes in the boron layer, then, after processing, oxygen will be able to reach the epi layer through those pinholes and may oxidize the surface of that layer.

In some embodiments, other layers can also be deposited on top of the boron layer during, or immediately following, step 111. These other layers may include anti-reflection coatings comprised of one or more materials, such as silicon dioxide, silicon nitride, magnesium fluoride, and lithium fluoride. These other layers may also include a protective layer comprising a thin (few nm) layer of a refractory metal. Even though the anti-reflection coating may be affected by DUV, VUV or EUV radiation, the presence of the boron layer between the anti-reflection coating and the epi layer shields the epi layer from charges and traps in the anti-reflection coating and ensures that the sensitivity of the image sensor does not significantly degrade.

In step 113, the front-side protective layer can be removed or patterned to prepare for fabrication of interconnects on the front surface. In some embodiments, this removal/patterning may include etching of the front-side surface in dilute HF, because the boron layer is relatively impervious to dilute HF.

In step 115, interconnects on the front surface can be patterned and fabricated. These interconnects may be formed by Al, Cu, or another metal. After interconnect fabrication is complete, a passivation layer may be deposited on the front-side surface to protect these interconnects.

In step 117, the completed circuit elements can be packaged. The package may include flip-chip bonding or wire bonding of a chip to a substrate. The package may include a window that transmits wavelengths of interest, or may comprise a flange or seal for interface to a vacuum seal. In electron-bombarded image sensor embodiments, the package may include other components such as a photocathode as well as a sealed, evacuated tube.

FIG. 2 illustrates an alternative exemplary technique 200 for fabricating an image sensor. In this embodiment, the circuit elements can be created in step 201 using standard semiconductor processing steps including lithography, deposition, ion implantation, annealing, and etching. In one embodiment, CCD and/or CMOS sensor elements and devices may also be created in step 201. These circuit elements are created in an epi layer on the front-side surface of the wafer. In preferred embodiments, the epi layer is about 20 µm to 40 µm thick. The epi layer has a low dopant concentration (p−). In one embodiment, interconnects, such as metal interconnects, can also be created in step 201.

In step 203, the front-side surface of the wafer can be protected. This protection may include depositing one or more protective layers on top of the circuit elements formed during step 201. This protection may also, or instead, include attaching the wafer to a handling wafer, such as a silicon wafer, a quartz wafer, or a wafer made of other material.

Step 205 involves thinning the wafer from the back-side so as to expose the epitaxial layer in, at least, the active sensor areas. This step may involve polishing, etching, or both. In some embodiments, the entire wafer is back-thinned. In other embodiments, only the active sensor areas are thinned all the way to the epitaxial layer.

Step 207 includes cleaning and preparing the back-side surface prior to the boron deposition. During this cleaning, the native oxide and any contaminants, including organics and metals, should be removed from the back-side surface. In one embodiment, this cleaning can be performed using a dilute HF solution or using an RCA clean process. After cleaning and during preparation, the wafer can be dried using the Marangoni drying technique or a similar technique to leave the surface dry and free of water marks.

In step 209, the wafer can be transported to a deposition tool in a protective environment, thereby allowing the wafer to be protected during step 211. In one embodiment, for example, the protective environment is a dry nitrogen atmosphere, which minimizes native oxide regrowth. The time spent to perform step 209 should be kept to a minimum, preferably no more than about five minutes.

In step 211, boron is deposited on the back-side surface of the wafer. In one preferred embodiment, this deposition can be done using a mixture of diborane and hydrogen gases at a temperature of about 400-450° C., thereby creating a high-purity amorphous boron layer. The thickness of the deposited boron layer depends on the intended application for the sensor. Typically, the boron layer thickness will be between about 2 nm and 10 nm. The minimum thickness is set by the need for a pinhole-free uniform film, whereas the maximum thickness depends on the absorption of the photons or charged particles of interest by the boron, as well as the maximum length of time that the wafer can be kept at the elevated temperature when there are metal interconnects on the front-side.

In some embodiments, other layers may be deposited on the boron layer in step 211. These other layers may include anti-reflection coatings comprised of one or more materials such as silicon dioxide, silicon nitride, magnesium fluoride and lithium fluoride. These other layers may also include a protective layer comprising a thin layer of a refractory metal. In some embodiments, this refractory metal layer thickness may be between approximately 1 nm and approximately 10 nm.

In one embodiment, the protective front-side layer may be removed in step 213. In another embodiment, in step 213, holes or vias can be opened in the protective front-side layer or through-silicon vias around the edges of the device can be exposed, thereby allowing connection to the circuit structures.

In step 215, the resulting structure may be packed in a suitable package. The packing step may comprise flip-chip bonding or wire bonding of the device to the substrate. The package may include a window that transmits wavelengths of interest, or may comprise a flange or seal for interface to a vacuum seal. In the electron-bombarded image sensor embodiments, the package may include other components such as the photocathode, and may comprise a sealed, evacuated tube.

Figure 3A:
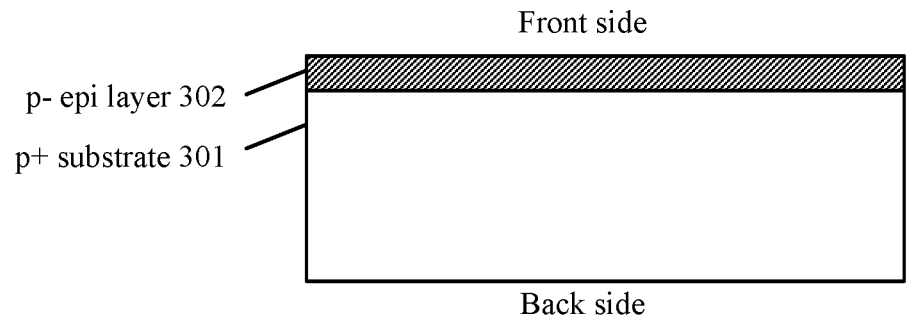
FIGS. 3A-3G illustrate exemplary cross-sections of a wafer subjected to the method described in reference to FIG. 1.
Figure 3B:
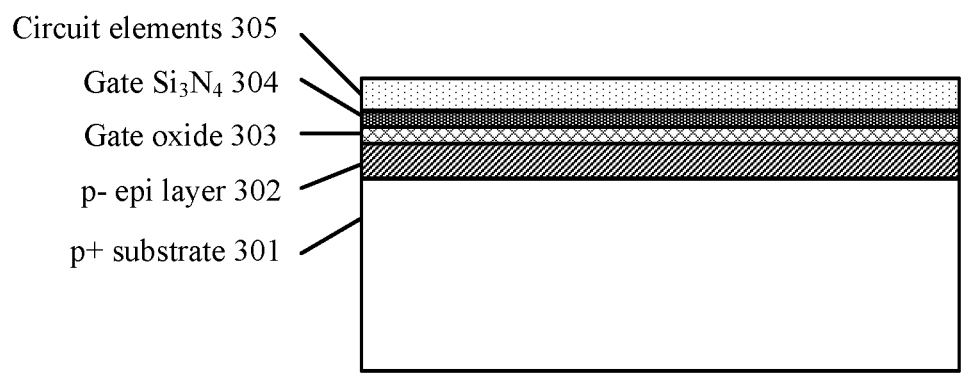
Figure 3C:
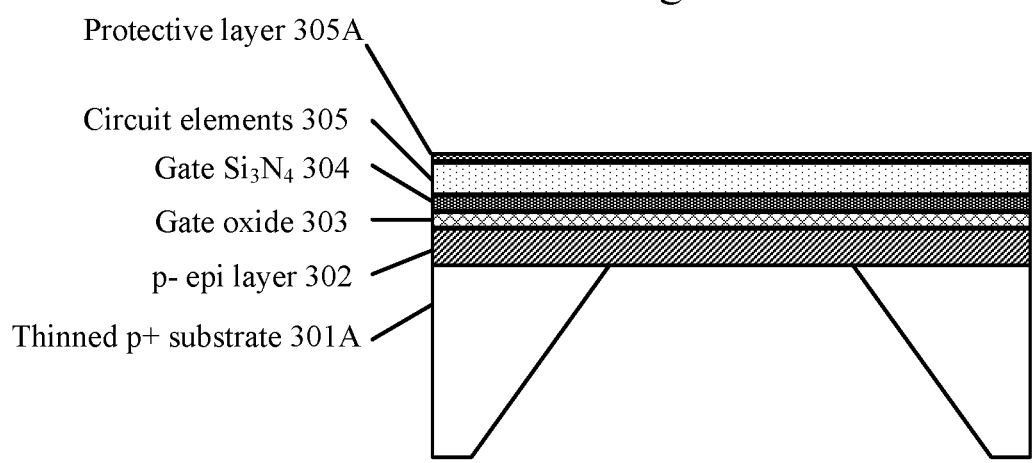
Figure 3D:
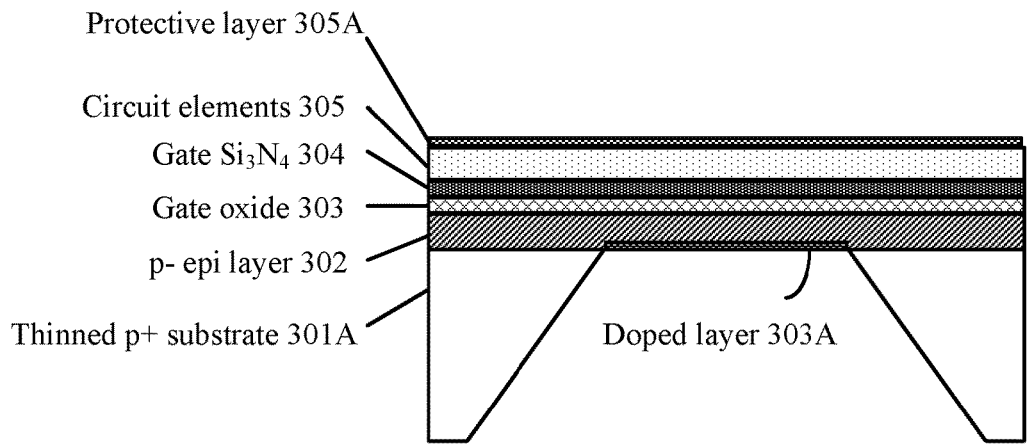
Figure 3E:
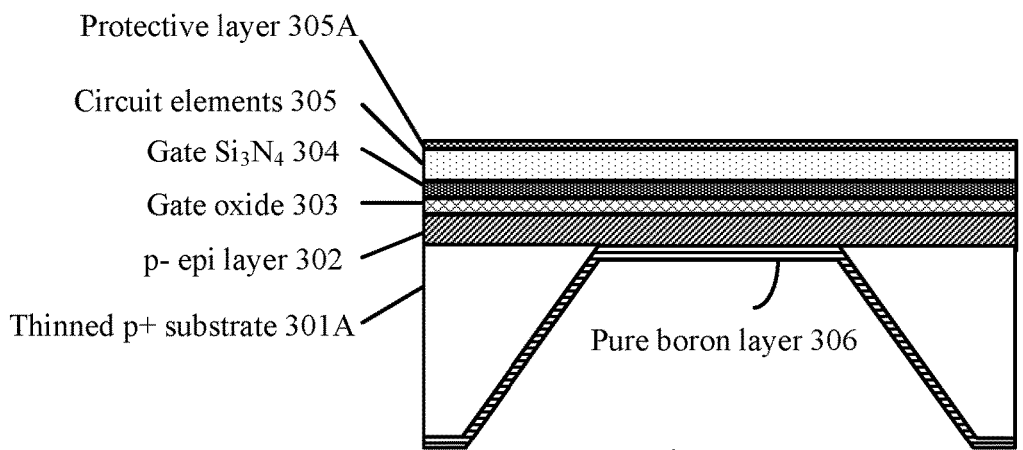
Figure 3F:
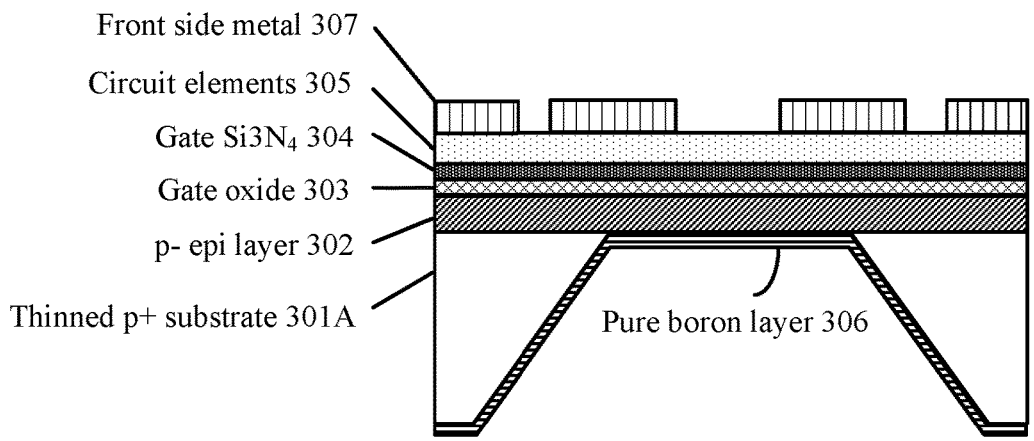
Figure 3G:
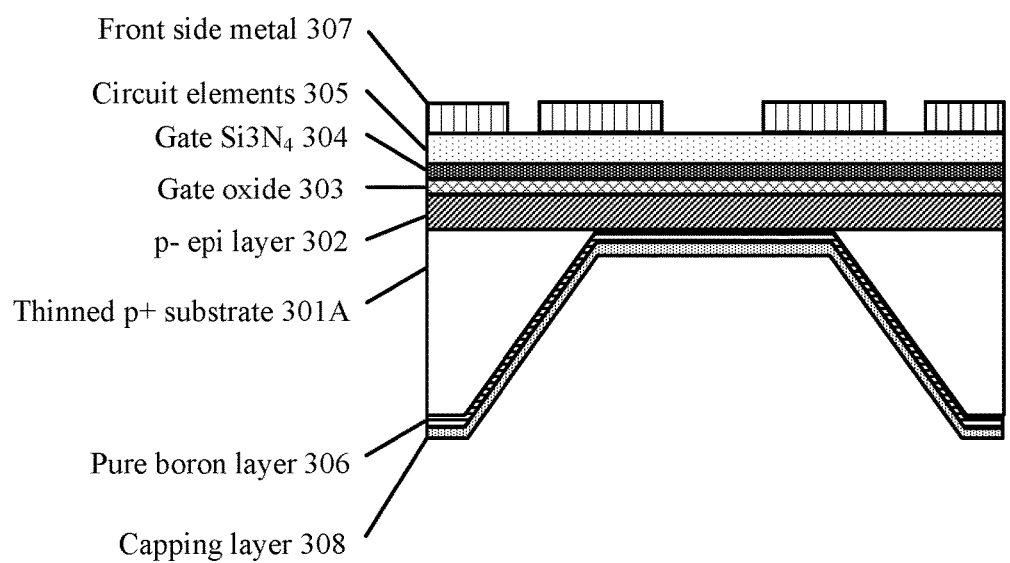

FIGS. 3A-3F illustrate exemplary cross-sections of a wafer subjected to method 100 (FIG. 1). FIG. 3A illustrates an epitaxial (epi) layer 302 being formed on the front side of a substrate 301. In one embodiment, substrate 301 is a p+ (i.e. highly p doped) substrate, and epi layer 302 is a p− epi layer (i.e. a layer with a low concentration of p dopant). FIG. 3B illustrates a gate oxide layer 303 being formed on epi layer 302, a silicon nitride ($Si_3N_4$) gate layer 304 being formed on gate oxide layer 303, and front-side circuit elements 305 being formed on gate layer 304 (step 101). Note that depending on the type of image sensor technology, the gate dielectric may comprise one, two, or three layers. Forming the front-side circuit elements includes implanting or doping portions of the front side of the epi layer and may involve patterning the gate layer. FIG. 3C illustrates substrate 301 being thinned at its back-side surface, at least in certain areas, to form thinned substrate 301A (step 103), and a protective layer 305A being formed on front-side circuit elements 305 (step 105). FIG. 3D illustrates an optional doped layer 302A that may be formed in a portion of epi layer 302 exposed by thinned substrate 301A. This doping may be formed by ion-implantation followed by thermal activation, by plasma doping, by plasma assisted doping or similar techniques. In one embodiment, this doping can be performed during step 107 as part of the back-side surface preparation and before high-temperature surface treatment in step 109. FIG. 3E illustrates a pure boron layer 306 being formed on thinned substrate 301A and exposed epi layer 302 (step 111). Since some of the boron diffuses a few nm into the epi layer, some embodiments do not need to include the separately doped layer 303A. FIG. 3F illustrates that after protective layer 305A is removed or opened (step 113), front-side metal (i.e. interconnect) 307 can be formed on front-side circuit elements 305. FIG. 3G illustrates one optional embodiment in which a capping layer 308 can be formed on boron layer 306. Capping layer 308 can be formed any time after step 111 (depositing the boron layer), but before step 117 (packaging).

Figure 4A:
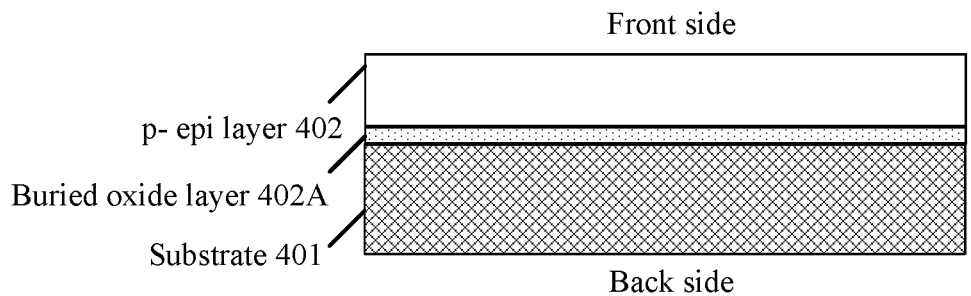
FIGS. 4A-4G illustrate exemplary cross-sections of a wafer subjected to the method described in reference to FIG. 2.
Figure 4B:
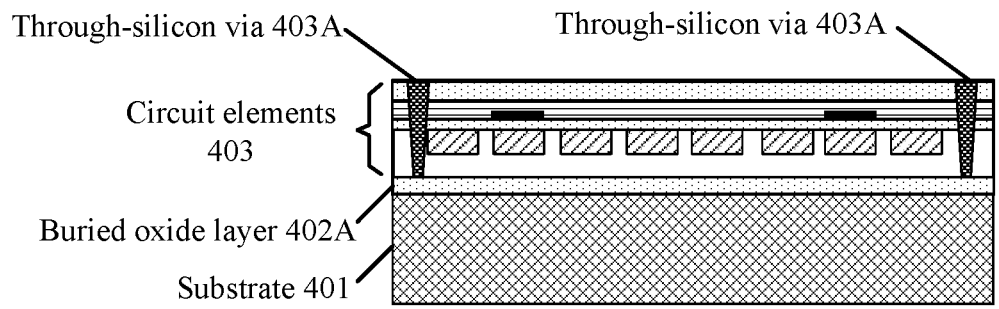
Figure 4C:
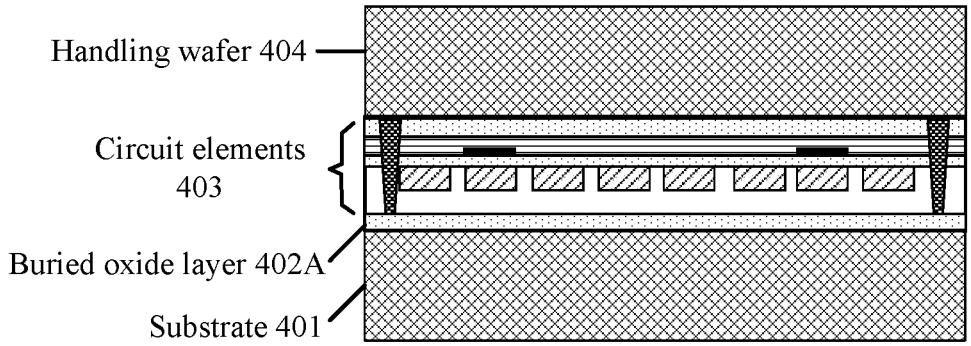
Figure 4D:
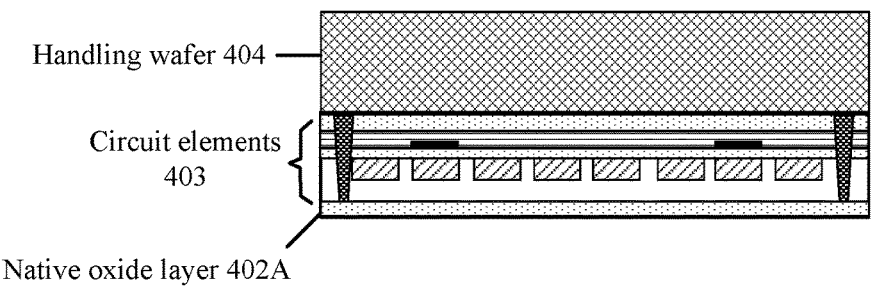
Figure 4E:
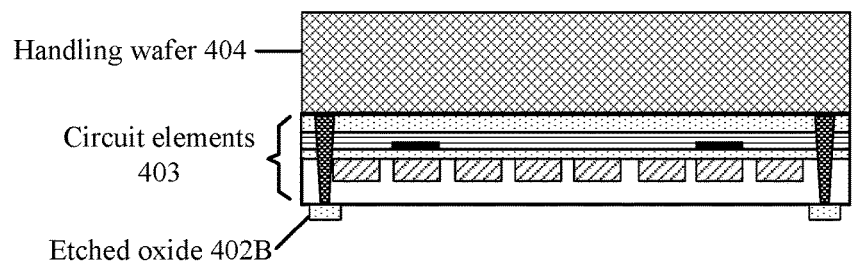
Figure 4F:
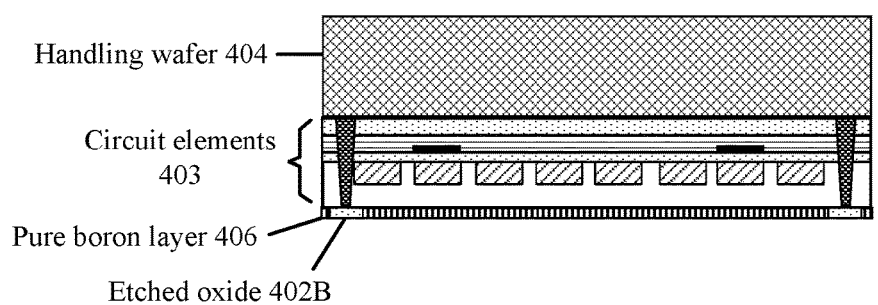
Figure 4G:
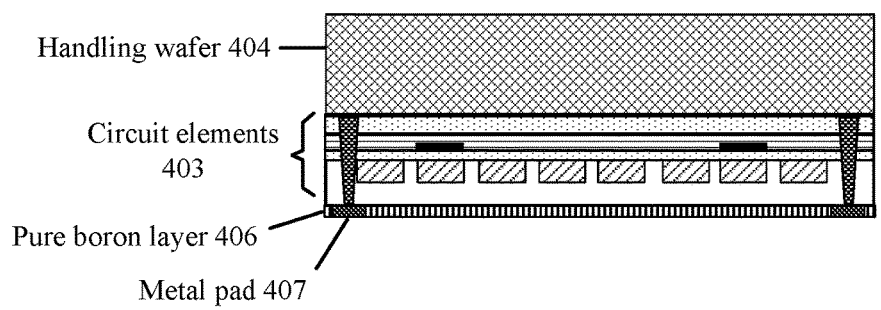

FIGS. 4A-4G illustrate exemplary cross-sections of a wafer subjected to method 120 (FIG. 1B). FIG. 4A illustrates an epitaxial (epi) layer 402 being formed on the front side of a substrate 401. In one embodiment, substrate 401 is a p+ substrate, and epi layer 402 is a p− epi layer. In one embodiment, the substrate is an SOI (silicon-on-insulator) wafer with a buried oxide layer 402A between substrate 401 and epi layer 402. SOI wafers are commercially available from Soitec (Bernin, France) and other suppliers. In other embodiments, the epi layer is grown directly on the substrate 401 without any buried oxide layer 402A. FIG. 4B illustrates various circuit elements 403 including interconnects that can be formed on the epi layer (step 121) (note that the epi layer is shown, but not labeled so as not to overly complicate the drawings). Because the interconnects are formed on the wafer prior to back thinning all the way to the epi layer, these interconnects can be formed using normal sub-micron CMOS processing techniques and may include multiple layers of high density metal interconnects. In some embodiments, multiple through-silicon vias (TSV) 403A are created around one, or more, edges of the image sensor array in order to allow connection to the circuit elements 403. FIG. 4C illustrates a handling wafer 404 attached to the top of the circuit elements 403 (step 123). Note that the through-silicon vias are shown, but not labeled so as not to overly complicate the drawings. In other embodiments, a protective layer can be used instead of handling wafer 404. FIG. 4D illustrates the wafer after substrate 401 is back-thinned to epi layer 402. In one embodiment, this back-thinning exposes buried oxide layer 402A. FIG. 4E illustrates the wafer after a cleaning and preparation of the back-side surface (step 127), which may result in etched oxide 402B being patterned so as to protect TSVs 403A while exposing the epi layer in the image sensor array areas. FIG. 4F illustrates a pure boron layer 406 after being formed on the back-side surface of the epi layer 402 (step 131). In some embodiments, an anti-reflection coating or metal coating or capping layer (not shown) may be deposited on top of the pure boron layer. FIG. 4G illustrates the wafer after etched oxide 402B is removed and replaced with metal pad 407 so as to allow electrical connection to the TSV 403A (step 131).

Figure 5:
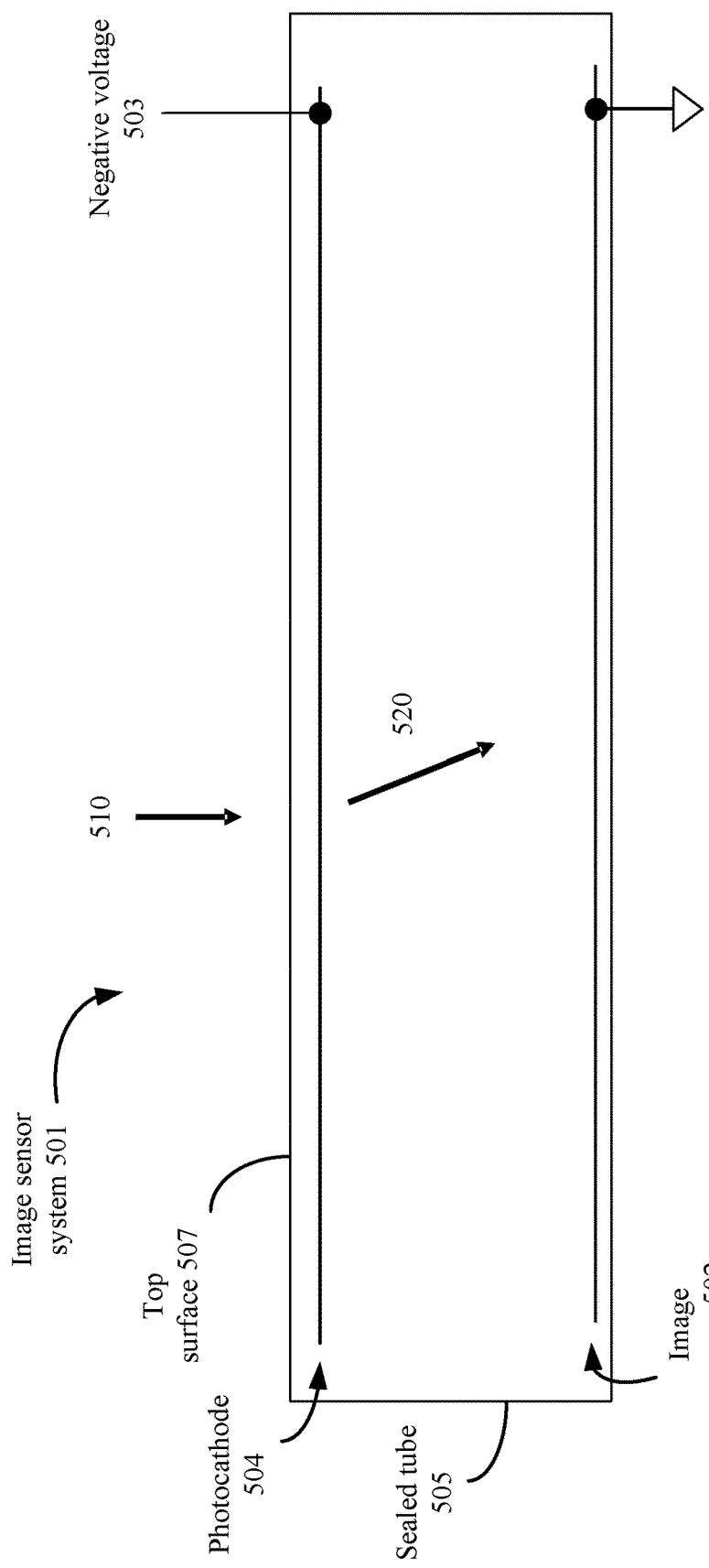
FIG. 5 illustrates an exemplary electron-bombarded image sensor system.

FIG. 5 illustrates an exemplary electron-bombarded image sensor system 501. In this embodiment, the whole assembly can be contained in a sealed tube 505 (e.g. substantially similar to the sealed tube of standard image intensifier and electron-bombarded CCD (EBCCD) devices). A top surface 507 of the tube 505 can include a window that is transparent at the wavelengths of interest. For UV sensitive electron-bombarded image sensors, this window preferably comprises a very pure grade of quartz, fused silica or alumina (sapphire). In some preferred embodiments, the outside surface of the window is coated with a UV anti-reflection coating. Such a coating might comprise a single layer of a low index material such as $MgF_2$, or might comprise a multi-layer coating.

Coated on the inside surface of the window, or placed immediately adjacent to that inside surface, is a photocathode 504. The photocathode material may be substantially similar to any photocathode material known in the art for use in photomultiplier, image intensifier, or prior-art EBCCD detectors. In preferred embodiments, the photocathode may comprise one or more alkali metals such as cesium, and/or may comprise a semiconductor such GaN, GaAs, or silicon. Photocathode 504 can be held at a negative voltage 503 relative to a solid-state image sensor 502, which is positioned near the bottom surface of sealed tube 505. In some embodiments, negative voltage 503 may be approximately 500 V; in other embodiments, it may be a few hundred volts or approximately 1000 V. In preferred embodiments, negative voltage 503 is between 100 V and 1500 V.

Solid-state image sensor 502 can be a thinned CCD or CMOS image sensor oriented so that the electrons impinge first on its back-side surface. The back-side of solid-state image sensor 502 includes a layer of boron deposited directly on the epi layer of the image array as described above. In some embodiments, a thin (few nm) layer of a conductive material, such as a refractory metal, is deposited on the boron layer to prevent charge-up of the sensor surface. A refractory metal such as titanium, tungsten, tantalum, rhodium, ruthenium, vanadium or chromium, has advantages compared with non-refractory metals because refractory metals' hardness makes them resistant to sputtering by the electrons, and they are relatively resistant to oxidation at room temperature. In some embodiments, solid-state image sensor 502 is a time-delay integration (TDI) CCD. In some embodiments, solid-state image sensor 502 comprises a linear array of electron-sensitive elements. In other embodiments, solid-state image sensor 502 comprises a two-dimensional array of electron sensitive elements. In some preferred embodiments, solid-state image sensor 502 is held close to ground potential (shown).

When light 510 is incident on the electron-bombarded image sensor system 501, one or more photoelectrons 520 are emitted from photocathode 504. These photoelectrons are emitted in substantially all directions, but they are accelerated towards solid-state image sensor 502 by the potential difference between photocathode 504 and solid-state image sensor 502. In preferred embodiments, the gap between photocathode 504 and solid-state image sensor 502 is less than 1 mm. In some embodiments, the gap is approximately 500 µm.

Incorporating solid-state image sensor 502 having one of the structures and/or fabricated in accordance with any of the methods described herein enables electron-bombarded image sensor system 501 to operate with a low potential difference between photocathode 504 and solid-state image sensor 502, and yet have high gain because electrons are more easily able to penetrate through the boron layer than through a silicon dioxide layer. Because boron-doped silicon, boron silicide, and boron are all at least partially conductive, charging of the surface under electron bombardment is minimized or avoided. The sensitivity to charge up can be further reduced by a conductive or metallic layer on top of the boron layer as described herein.

In prior art EBCCD sensors, the gap between the photocathode and the image sensor is typically 1-2 mm. Such a large gap allows significant transverse motion of the electrons as they travel from the photocathode to the image sensor due to energy of the electrons as they emerge from the photocathode. A gap of 1-2 mm or more is necessary because of the large potential difference between the photocathode and the image sensor (typically about 2000 V or more). Reducing the potential difference between the photocathode and the image sensor allows a smaller gap to be used. Furthermore, the lower energy of the electrons means that there is less spreading of the electrons created within the solid-state image sensor.

The low energy of the electrons arriving at solid-state image sensor 502 means that the probability of atoms being ablated from the surface of solid-state image sensor 502 is low to zero. Furthermore, the energy of the electrons arriving at solid state image sensor 502 is not enough to generate X-rays from the silicon, thereby avoiding the generation of spurious signal in nearby pixels of image sensor 502.

Collisions of low energy electrons with residual gas atoms in the vacuum created in sealed tube 505 will generate fewer ions as compared with high energy electrons. Furthermore, due to the low potential difference between photocathode 504 and solid-state image sensor 502, those ions will have less kinetic energy when they strike the photocathode and will ablate less photocathode material.

Additional details of electron-bombarded image sensors that can be incorporated into the electron-bombarded image sensor 501 can be found in U.S. patent application Ser. No. 13/710,315, entitled "ELECTRON-BOMBARDED CHARGE-COUPLED DEVICE AND INSPECTION SYSTEMS USING EBCCD DETECTORS", filed by Chuang et al. on Dec. 10, 2012 (published on Jun. 13, 2013 as 2013/0148112), and incorporated by reference herein. A photocathode structure suitable for use in electron-bombarded image sensor system 501 is described in U.S. Provisional Patent Application 61/679,200 entitled "PHOTOCATHODE WITH LOW NOISE AND HIGH QUANTUM EFFICIENCY, HIGH SPATIAL RESOLUTION LOW-NOISE IMAGE SENSOR AND INSPECTION SYSTEMS INCORPORATING AN IMAGE SENSOR", filed by Chuang et al. on Aug. 3, 2012, and incorporated by reference herein.

Figure 6:
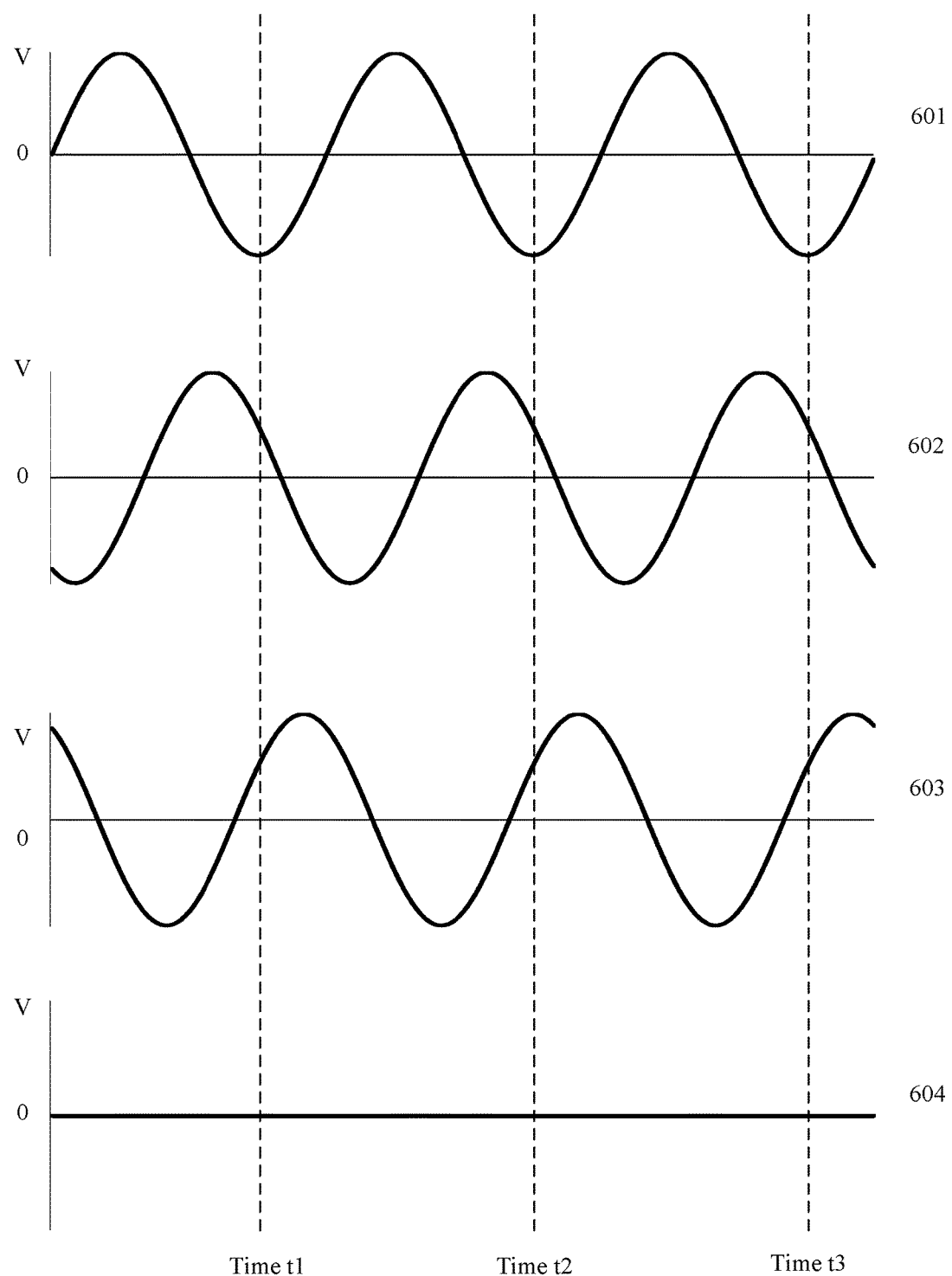
FIG. 6 illustrates exemplary driving voltages for the clock signals of any of the image sensors described herein that incorporate CCDs.

FIG. 6 illustrates exemplary driving voltages for the clock signals of any of the image sensors described herein that incorporate CCDs. In a CCD, charge needs to be transferred from one storage element to another until the charge reaches the output amplifier. Multiple clock signals are needed to transfer the charge. Depending on the design of the CCD, typically 2, 3 or 4 clock signals are needed. In some preferred embodiments, those clock signals are sinusoidal, or substantially sinusoidal, in shape, in preference to substantially square waveforms used in traditional CCD devices. The advantages of using sinusoidal waveforms are that the charge transfer is smoother (which is particularly an advantage in allowing TDI sensors to track the motion of the image more accurately), and the clock signals generate less electrical noise and heat because of the minimal content of harmonics of the fundamental frequency. FIG. 6 illustrates the clock voltages for a 3-phase CCD. Clock signal 601 shows the voltage on the first clock signal as a function of time. Clock signal 601 is a substantially sinusoidal waveform. The second clock signal 602 also has a voltage that varies as a function of time, but is substantially 120° phase-delayed with respect to clock signal 601. The voltage of the third clock signal 603 also varies as a function of time, but is substantially 120° phase-delayed with respect to clock signal 602, and hence substantially 240° phase-delayed with respect to clock signal 601. Line 604 illustrates the sum of the three clock signals 601, 602, and 603, which is substantially zero all the time. The substantially zero sum voltage means that little current from the clock signals flows in the ground signal of solid-state image sensor 502, thereby resulting in lower electrical noise levels. This is in contrast to the sum of three out-of-phase square-wave clock signals, which would have non-zero sums voltages essentially all the time.

In an image sensor including a 2-phase CCD (not shown), the two clock signals would be substantially 180° out of phase with one another. In a 4-phase CCD (not show), the second clock signal would be substantially 90° phase-delayed with respect to the first clock signal, the third clock signal would be substantially 180° phase-delayed with respect to the first clock signal, and the fourth clock signal would be substantially 270° phase-delayed with respect to the first clock signal.

More details of the use of sinusoidal and other clock signals for driving CCD image sensors can be found in U.S. Pat. No. 7,952,633, entitled "Apparatus for continuous clocking of TDI sensors" by Brown et al., which issued May 31, 2011, and in U.S. Pat. No. 7,609,309, entitled "Continuous clocking of TDI sensors" by Brown et al., which issued Oct. 27, 2009. Both of these patents are incorporated by reference herein.

Figure 7A:
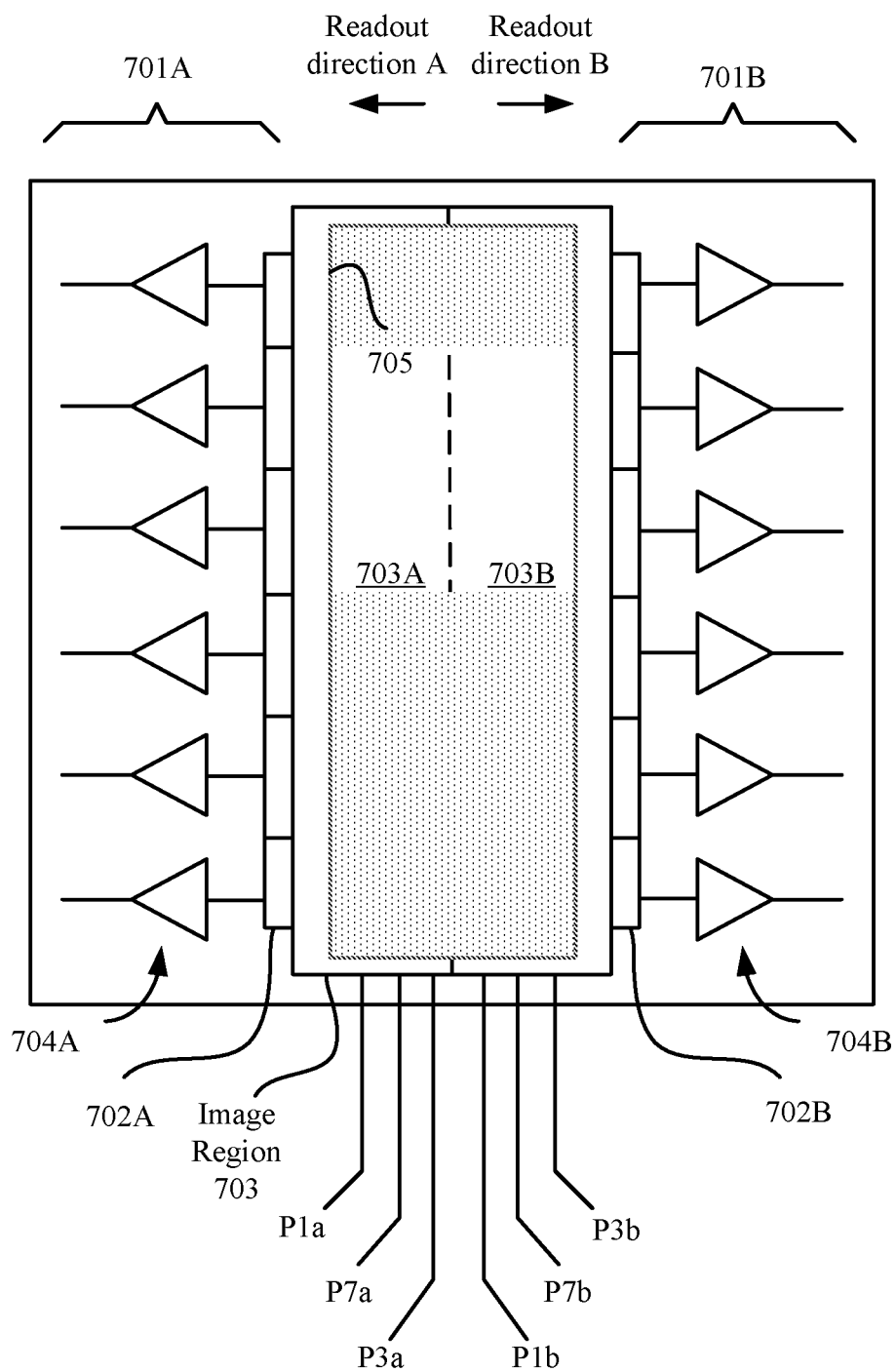
FIG. 7A illustrates an exemplary split-readout image sensor including two sets of readout circuits.

FIG. 7A illustrates an exemplary split-readout image sensor 700 including two sets of readout circuits 701A and 701B positioned on either side of an image region 703. Image region 703 includes a pure boron layer on its light sensitive surface as described herein. Readout circuits 701A and 701B can include serial registers 702A and 702B and readout amplifiers 704A and 704B, as well as other components such as transfer gates. Exemplary embodiments of readout circuits 701A and 701B, as well as other components of sensor 700 are described in U.S. Pat. No. 7,609,309, entitled "Continuous Clocking of TDI Sensors", issued Oct. 27, 2009, which is incorporated by reference herein. Image region 703 is a two-dimensional (2D) array of pixels, and each line of the image is read out concurrently in each direction A and B. Each line is then read out one pixel at a time in the simplest case. Therefore, in preferred embodiments, the serial registers 702A and 702B can be divided into a plurality of register segments (e.g. FIG. 7A shows each serial register being divided into six segments, thereby allowing parallel read out using a plurality of amplifiers 704A and 704B.

Notably, readout circuits 701A and 701B can be operated independently, thereby allowing image sensor 700 to provide two readout directions A and B. In a split-readout mode, each side of image region 703 (i.e. sides 703A and 703B) can be synchronously clocked to read out one image line into their respective output channels. In one embodiment, image region 703 may have 1000 lines, each line formed by a column of pixels. Therefore, during the split-readout mode, 500 lines could be read out in direction A and, concurrently, 500 lines could be read out in direction B.

Figure 7B:
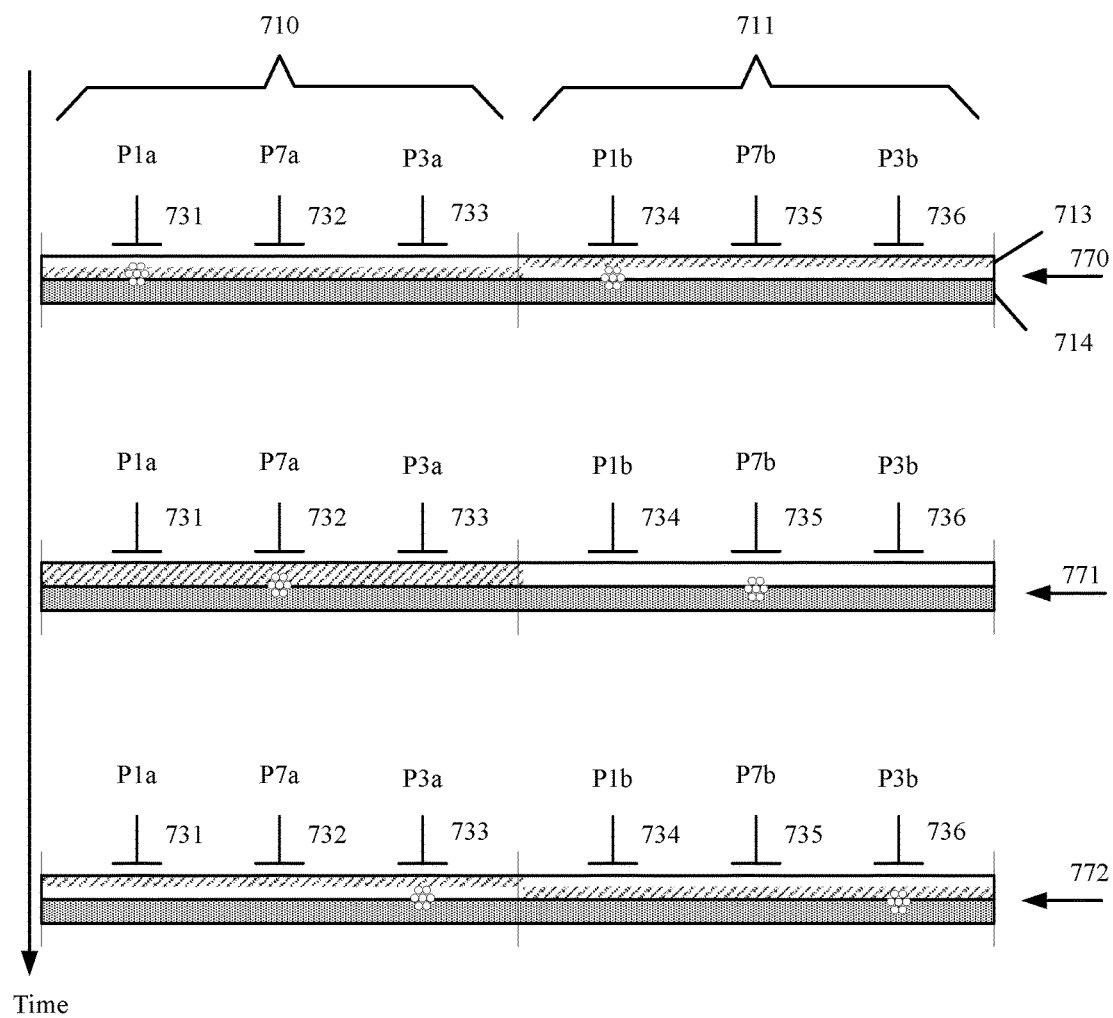
FIG. 7B illustrates a plurality of CCD drivers driving sets of gate electrodes, each set having multiple gates.

This split-readout mode is possible based on the timed activation of the charge-coupled device (CCD) drivers in the image sensor. For example, a plurality of CCD drivers P1*a*, P2*a*, P3*a*, P1*b*, P2*b*, and P3*b* can be used to provide phases. As shown in FIG. 7B, CCD drivers P1*a*, P2*a*, P3*a*, P1*b*, P2*b*, and P3*b* can be characterized as driving sets of gate electrodes (hereinafter gates), each set having six gates. In one preferred embodiment of the image sensor, three gates are provided for each pixel to provide three phases. In FIG. 7B, two pixels 710 and 711 are shown, wherein gates 731, 732, and 733 are positioned over pixel 710 and gates 734, 735, and 736 are positioned over pixel 711. In the image sensor, pixels 710 and 711 are aligned along the read-out axis to form part of a column of the 2D array of pixels forming image region 703.

Image region 703 can be implemented as an optical sensor or a charged particle sensor. In one optical sensor embodiment, image region 703 can include a photo-sensitive p-type silicon substrate 714 and an n-type buried channel 713. The electrostatic forces in silicon substrate 714 are determined by the voltage level applied to a particular gate by a clock input signal (e.g. one of clock signals from CCD drivers P1*a*, P2*a*, P3*a*, P1*b*, P2*b*, and P3*b*). High level voltages induce the formation of a potential "well" beneath the gate, whereas low level voltages form a potential barrier to electron movement. To ensure that charge from one pixel is not mixed with other pixels, a gate voltage is driven high when an adjacent gate voltage is driven low. At an initial state at time 770, gates 731 and 734 of pixels 710 and 711, respectively, have high level voltages that form potential wells with integrated charge (i.e. electrons), and gates 732, 733 (of pixel 710) and 735, 736 (of pixel 711) have low level voltages that form potential barriers. At a subsequent time 721, gates 732 and 735 of pixels 710 and 711, respectively, have high level voltages that form potential wells with integrated charge (i.e. electrons), and gates 731, 733 (of pixel 710) and 734, 736 (of pixel 711) have low level voltages that form potential barriers. At yet a subsequent time 771, gates 733 and 736 of pixels 710 and 711, respectively, have high level voltages that form potential wells with integrated charge (i.e. electrons), and gates 731, 732 (of pixel 710) and 734, 735 (of pixel 711) have low level voltages that form potential barriers. Note that adjacent gates when shifting charge preferably both have a high level voltage for a short time to facilitate charge transfer. Thus from time 770 to time 771, the charge is shifted from left to right, i.e. from pixel 710 to pixel 711. A similar directional shifting of charge can be take place from time 771 to time 772.

Additional details of split-readout image sensor 700 are provided in U.S. Provisional Patent Application 61/735,427, entitled "METHOD AND APPARATUS FOR HIGH SPEED ACQUISITION OF MOVING IMAGES USING PULSED ILLUMINATION", filed by David Brown et al. on Dec. 10, 2012, and incorporated by reference herein. Additional details regarding other exemplary image sensors are provided in U.S. Pat. No. 7,528,943 entitled "METHOD AND APPARATUS FOR SIMULTANEOUS HIGH-SPEED ACQUISITION OF MULTIPLE IMAGES" by Brown et al., issued May 5, 2009, and incorporated by reference herein.

Figure 8:
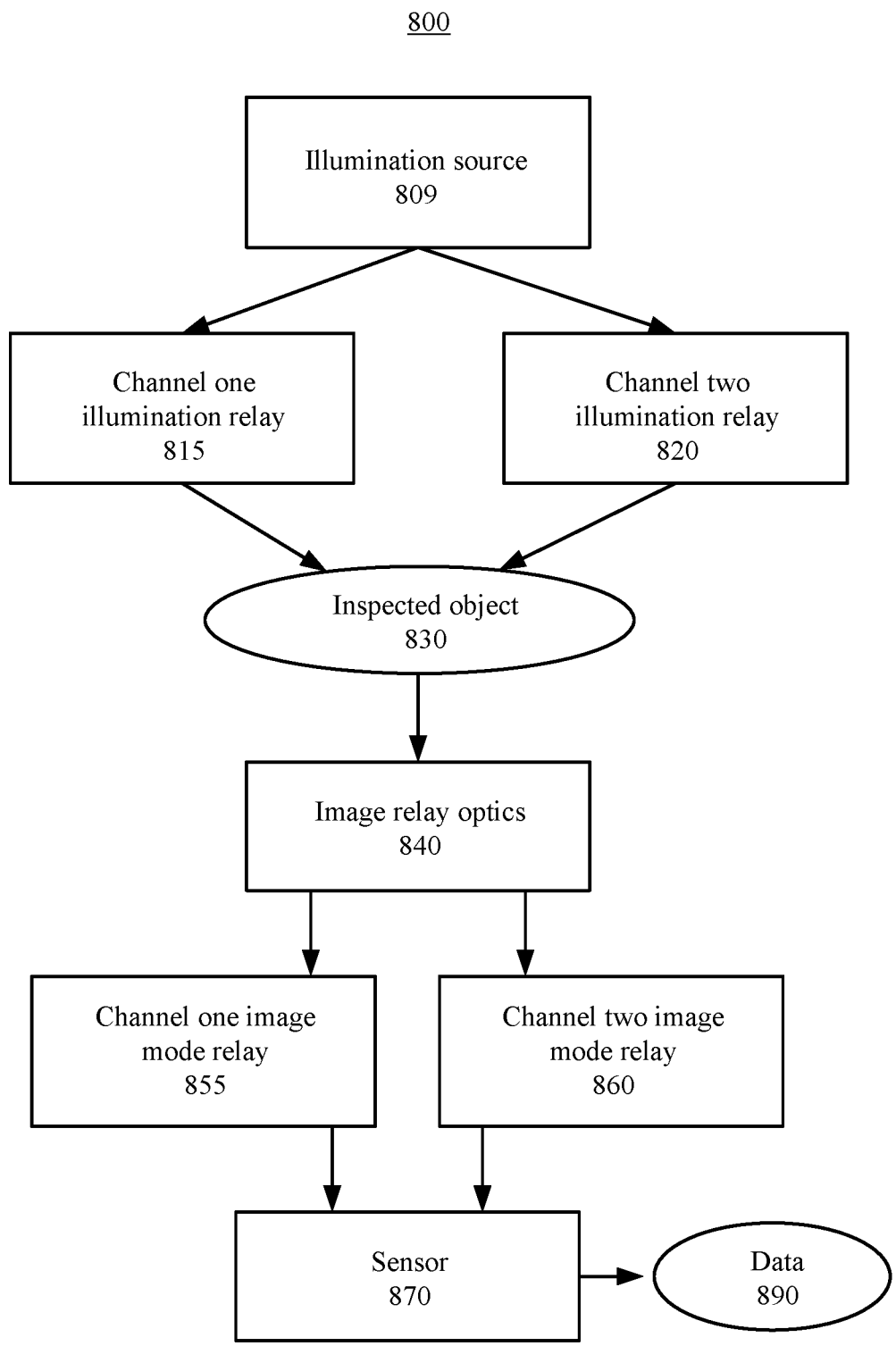
FIG. 8 shows a reticle, photomask or wafer inspection system that can simultaneously detect two channels of image or signal on one sensor.

FIG. 8 shows a reticle, photomask or wafer inspection system 800 that simultaneously detects two channels of image or signal on one sensor 870. Image sensor 870 comprises a split-readout image sensor as described above. Illumination source 809 may incorporate a 193 nm or sub-200-nm laser. The two channels may comprise reflected and transmitted intensity when an inspected object 830 is transparent (for example a reticle or photomask), or may comprise two different illumination modes, such as angles of incidence, polarization states, wavelength ranges or some combination thereof. The light is directed to inspected object 830 using channel one illumination relay 815 and channel two illumination relay 820.

The inspected object 830 may be a reticle, a photomask, a semiconductor wafer or other article to be inspected. Image relay optics 840 can direct the light that is reflected and/or transmitted by inspected object 830 to a channel one image mode relay 855 and to a channel two image mode relay. Channel one image mode relay 855 is tuned to detect the reflection/transmission corresponding to channel one illumination illumination relay 815, whereas channel two image mode relay sensor 860 is tuned to detect the reflection/transmission corresponding to channel two illumination relay 820. Channel one image mode relay 855 and channel two image mode relay sensor 860 in turn direct their outputs to sensor 870. The data corresponding to the detected signals or images for the two channels is shown as data 890 and is transmitted to a computer (not shown) for processing.

Other details of reticle and photomask inspection systems and methods that may be configured to measure transmitted and reflected light from a reticle or photomask are described in U.S. Pat. No. 7,352,457, which issued to Kvamme et al. on Apr. 1, 2008, and in U.S. Pat. No. 5,563,702, which issued to Emery et al. on Oct. 8, 1996, both of which are incorporated by reference herein.

Figure 9:
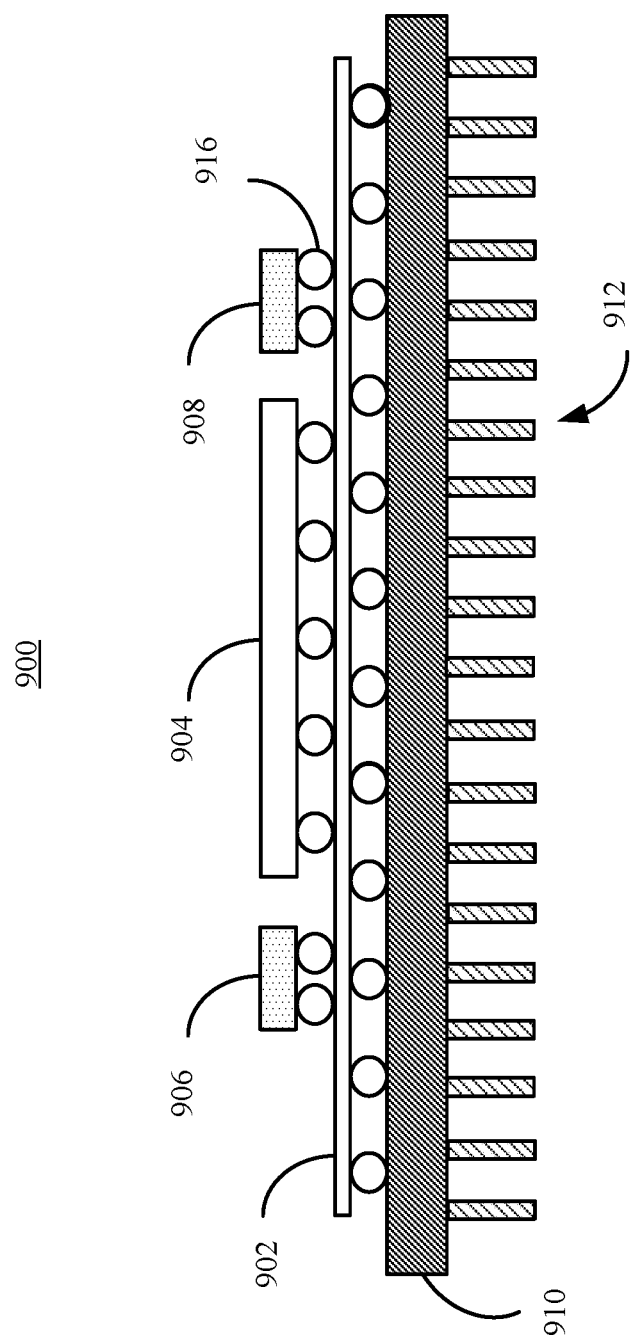
FIG. 9 illustrates an exemplary detector assembly incorporating an image sensor, a silicon interposer, and other electronics.

FIG. 9 illustrates an exemplary detector assembly 900 incorporating an image sensor 904, a silicon interposer 902 and other electronics in accordance with certain embodiments of the present invention.

In one aspect of the present invention, the detector assembly 900 may include one or more light sensitive sensors 904 disposed on the surface of an interposer 902. In some embodiments, the one or more interposers 902 of the assembly 100 may include, but are not limited to, a silicon interposer. In a further aspect of the present invention, the one or more light sensitive sensors 904 of the assembly 900 are back-thinned and further configured for back-illumination including a boron layer deposited on the back surface as described above.

In another aspect of the present invention, various circuit elements of the assembly 900 may be disposed on or built into the interposer 902. In one embodiment, one or more amplification circuits (e.g., charge conversion amplifier) (not shown) may be disposed on or built into the interposer 902. In another embodiment, one or more conversion circuits 908 (e.g., analog-to-digital conversion circuits, i.e. digitizers 908) may be disposed on or built into the interposer 902. In another embodiment, one or more driver circuits 906 may be disposed on or built into the interposer 902. For example, the one or more driver circuits 906 may include a timing/serial drive circuit. For instance, the one or more driver circuits 906 may include, but are not limited to, clock driver circuitry or reset driver circuitry. In another embodiment, one or more decoupling capacitors (not shown) may be disposed on or built into the interposer 902. In a further embodiment, one or more serial transmitters (not shown in FIG. 9) maybe disposed on or built into the interposer 102.

In another aspect of the present invention, one or more support structures may be disposed between the bottom surface of the light sensitive array sensor 904 and the top surface of the interposer 902 in order to provide physical support to the sensor 904. In one embodiment, a plurality of solder balls 916 may be disposed between the bottom surface of the light sensitive array sensor 904 and the top surface of the interposer 902 in order to provide physical support to the sensor 904. It is recognized herein that while the imaging region of the sensor 904 might not include external electrical connections, the back-thinning of the sensor 904 causes the sensor 904 to become increasingly flexible. As such, solder balls 916 may be utilized to connect the sensor 904 to the interposer 902 in a manner that reinforces the imaging portion of the sensor 904. In an alternative embodiment, an underfill material may be disposed between the bottom surface of the light sensitive array sensor 904 and the top surface of the interposer 902 in order to provide physical support to the sensor 904. For example, an epoxy resin may be disposed between the bottom surface of the light sensitive array sensor 904 and the top surface of the interposer 902.

In another aspect of the present invention, the interposer 902 and the various additional circuitry (e.g., amplification circuit, driver circuits 906, digitizer circuits 908, and the like) are disposed on a surface of a substrate 910. In a further aspect, the substrate 910 includes a substrate having high thermal conductivity (e.g., ceramic substrate). In this regard, the substrate 910 is configured to provide physical support to the sensor 904/interposer 902 assembly, while also providing a means for the assembly 900 to efficiently conduct heat away from the imaging sensor 904 and the various other circuitry (e.g., digitizer 906, driver circuitry 908, amplifier, and the like). It is recognized herein that the substrate may include any rigid highly heat conductive substrate material known in the art. For example, the substrate 910 may include, but is not limited to, a ceramic substrate. For instance, the substrate 110 may include, but is not limited to, aluminum nitride.

In another embodiment, the substrate 910 may be configured to provide an interface to a socket or an underlying printed circuit board (PCB). For example, as shown in FIG. 9, the substrate 910 may provide interconnection between the interposer 902 and a socket or a PCB via interconnects 912. Those skilled in the art will recognize that the substrate 910 may be operatively coupled to an underlying PCB and further electrically coupled to a socket or PCB in a variety of ways, all of which are interpreted to be within the scope of the present invention.

More details of detector assemblies incorporating image sensors, silicon interposers, and other electronics can be found in U.S. Pat. No. 8,748,828, entitled "INTERPOSER BASED IMAGING SENSOR FOR HIGH-SPEED IMAGE ACQUISITION AND INSPECTION SYSTEMS", filed by Brown et al. issued Jun. 10, 2014, and incorporated by reference herein.

Figure 10:
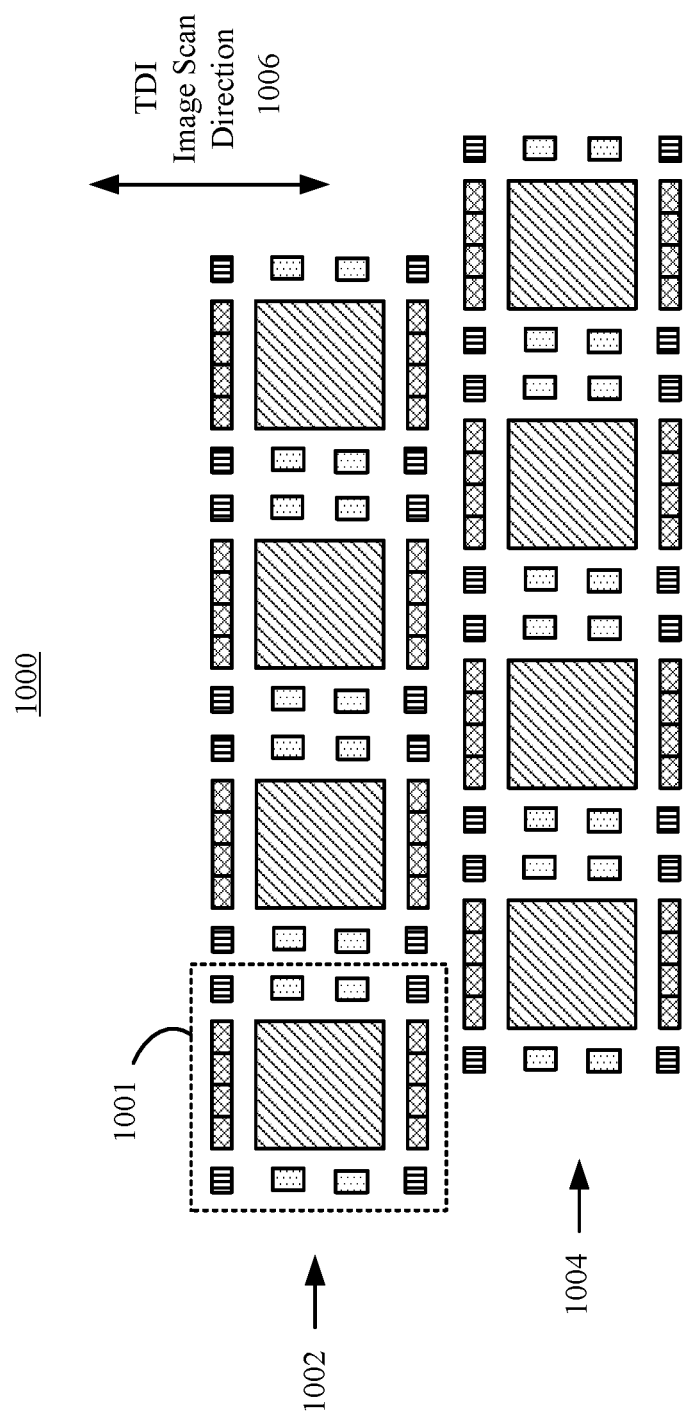
FIG. 10 illustrates an exemplary sensor module array including a plurality of time delay integration (TDI) sensor modules.

FIG. 10 illustrates an exemplary sensor module array 1000 including a plurality of time delay integration (TDI) sensor modules 1001. Each sensor module 1001 includes one of the above-described image sensors. In some embodiments, the image sensors may have a few nm (such as 1 or 2 nm) thick coating of Ru or other refractory metal on top of the boron in order to protect the boron during cleaning. In one embodiment, each TDI sensor module 1001 can include localized driving and signal processing circuitry. This circuitry can include a TDI sensor (the center block), processing circuits for processing the signals from the TDI sensor, timing and serial drive circuits, and pixel gate driver circuits. The driving/processing circuits are positioned around the TDI sensor. Thus, the TDI sensors in adjacent rows can be aligned such that at least 100% image coverage is achieved when used in a continuous scanning configuration.

For example, in the embodiment shown in FIG. 10, the upper row 1002 can be offset with respect to the lower row 1004 such that the TDI sensor is positioned in the gap produced by the driving/processing circuits of an adjacent row. To ensure no gaps in image coverage, the width of each TDI sensor is equal to or greater than the space between TDI sensors. In this configuration, as the inspected wafer/mask/reticle is being moved in a TDI image scan direction 1006, sensor module array 1000 can ensure 100% EUV wavelength image capture. In one embodiment, some minimal overlap between TDI sensors from adjacent rows can provide redundant data. This redundant data can, for example, ensure accurate alignment of the image data generated by TDI sensor modules 1001. In one embodiment of minimal overlap, the inspection system can arbitrarily select the data from one TDI sensor module to be used for the edge pixels. In another embodiment, a detection system can combine and align, using sub-pixel digital processing, the data from multiple TDI sensor modules, to achieve improved quality data near edge pixels.

More details of detector arrays for a EUV inspection system are described in U.S. Pat. No. 8,553,217, entitled "EUV HIGH THROUGHPUT INSPECTION SYSTEM FOR DEFECT DETECTION ON PATTERNED EUV MASKS, MASK BLANKS, AND WAFERS", by Chuang et al., issued on Oct. 8, 2013, and incorporated by reference herein.

Figure 11:
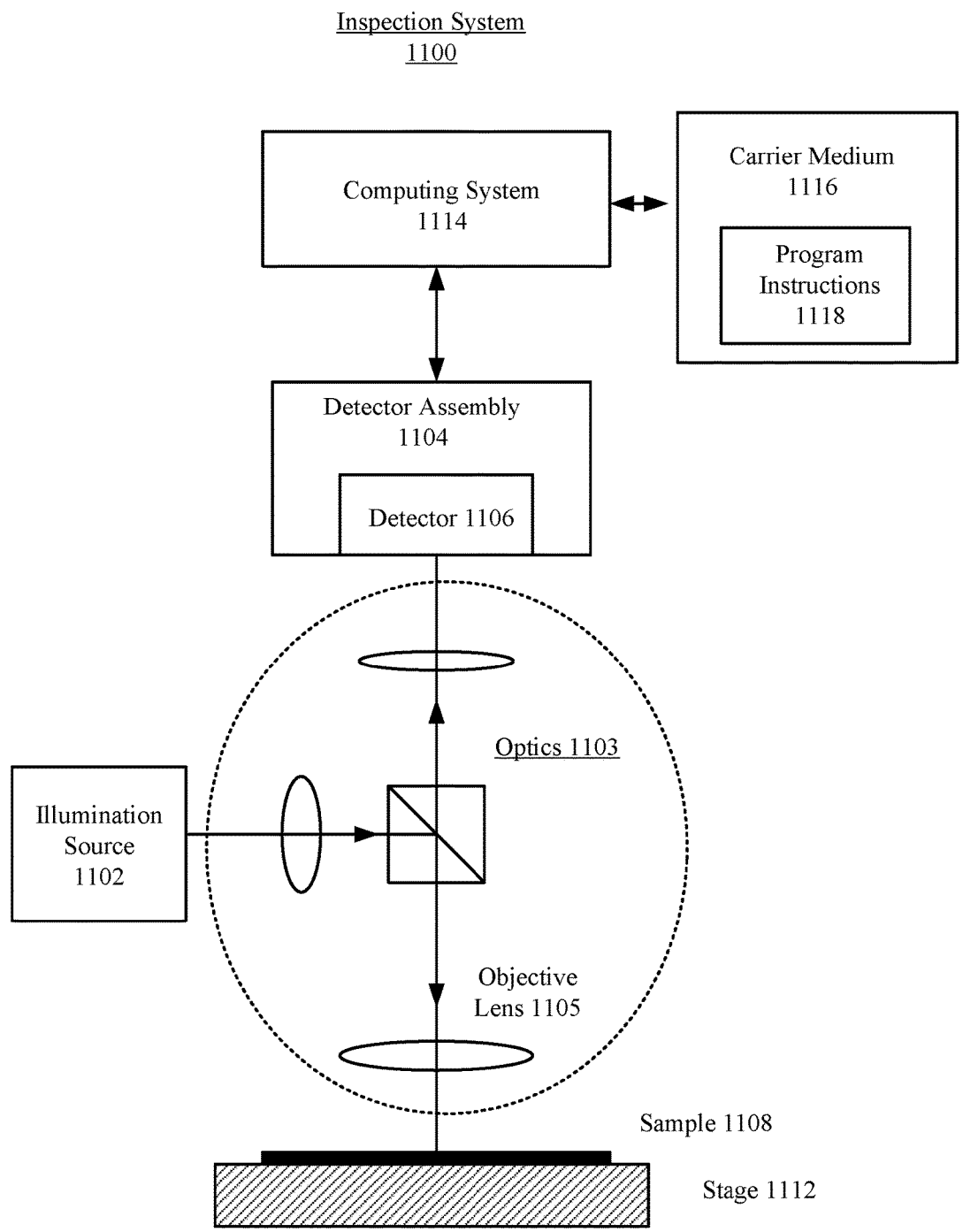
FIG. 11 illustrates an exemplary inspection system configured to measure a sample such as a wafer, reticle, or photomask.

FIG. 11 illustrates an exemplary inspection system 1100 configured to measure a sample 1108 such as a wafer, reticle, or photomask. Sample 1108 is placed on a stage 1112 in facilitate movement to different regions of sample 1108 underneath the optics. Stage 1112 may comprise an X-Y stage or an R-θ stage. In some embodiments, stage 1112 can adjust the height of sample 1108 during inspection to maintain focus. In other embodiments, an objective lens 1105 can be adjusted to maintain focus.

An illumination source 1102 may comprise one or more lasers and/or a broad-band light source. Illumination source 1102 may emit DUV and/or VUV radiation. Optics 1103 including an objective lens 1105 can direct that radiation towards, and focuses it on, sample 1108. Optics 1103 may also comprise mirrors, lenses, and/or beam splitters. Light reflected or scattered from sample 1108 can be collected, directed, and focused by optics 1103 onto a detector 1106, which is within a detector assembly 1104.

Detector 1106 may include one, or more, of the image sensors described herein, including boron-coated back-illuminated CCD sensors, boron-coated back-illuminated CMOS sensors, and electron-bombarded images sensors incorporating a boron-coated back-thinned solid state image sensor. Detector 1106 may include a two-dimensional array sensor or a one-dimensional line sensor. In one embodiment, the output of detector 1106 can be provided to a computing system 1114, which analyzes the output. Computing system 1114 can be configured by program instructions 1118, which can be stored on a carrier medium 1116.

In one embodiment, illumination source 1102 may be a continuous source such as an arc lamp, a laser-pumped plasma light source, or a CW laser. In another embodiment, illumination source 1102 may be a pulsed source such as a mode-locked laser, a Q-switched laser, or a plasma light source pumped by a Q-switched laser. In some embodiments of inspection system 1100 incorporating a Q-switched laser, the image sensor or sensors within detector 1106 are synchronized with the laser pulses. In such embodiments, the image sensor may operate in a TDI mode during the laser pulse and then may readout the data through multiple outputs on both sides of the sensor in between laser pulses.

Some embodiments of inspection system 1100 illuminate a line on sample 1108, and collect scattered and/or reflected light in one or more dark-field and/or bright-field collection channels. In such embodiments, the image sensor may be a line sensor or an electron-bombarded line sensor.

Some embodiments of inspection system 1100 illuminate multiple spots on sample 1108, and collect scattered and/or reflected light in one or more dark-field and/or bright-field collection channels. In such embodiments, the image sensor may be a two-dimensional array sensor or an electron-bombarded two-dimensional array sensor.

Additional details of various embodiments of inspection system 1100, incorporating one or more images described herein, can be found in U.S. Provisional Application 61/506,892, entitled "SAMPLE INSPECTION SYSTEM", filed on Jul. 12, 2011 by Romanovsky et al., U.S. Published Patent Application 2013/0016346, entitled "WAFER INSPECTION", which published on Jan. 17, 2013 by Romanovsky et al., U.S. Published Patent Application 2009/0180176, by Armstrong et al., which published on Jul. 16, 2009, U.S. Published Patent Application 2007/0002465 by Chuang et al., which published on Jan. 4, 2007, U.S. Pat. No. 5,999,310, by Shafer et al., which issued on Dec. 7, 1999, and U.S. Pat. No. 7,525,649 by Leong et al., which issued on Apr. 28, 2009. All of these patents and patent applications are incorporated by reference herein.

The various embodiments of the structures and methods of this invention that are described above are illustrative only of the principles of this invention and are not intended to limit the scope of the invention to the particular embodiments described. For example, additional steps may be added to the flow charts depicted in FIGS. 1 and 2, or some of the steps shown may be done in different sequence than shown. Thus, the invention is limited only by the following claims and their equivalents.

The invention claimed is:

1. An image sensor for sensing at least one of deep ultraviolet (DUV) radiation, vacuum ultraviolet (VUV) radiation, extreme ultraviolet (EUV) radiation, and charged particles, the image sensor comprising:
   a silicon membrane comprising an epitaxial layer including opposing first and second surfaces;
   one or more circuit elements formed on the first surface of the epitaxial layer;
   a doped layer formed in the second surface of the epitaxial layer; and
   a pure boron layer disposed on the second surface of the epitaxial layer,
   wherein the pure boron layer is between 2 nm and 20 nm thick.

2. The image sensor of claim 1, wherein the epitaxial layer is between 20 μm and 40 μm thick.

3. The image sensor of claim 2, further comprising an anti-reflection coating deposited on the boron layer.

4. The image sensor of claim 2, further comprising a conductive coating deposited on the boron layer to form a capping layer.

5. The image sensor of claim 1, further comprising a handling wafer attached to the circuit elements.

6. The image sensor of claim 5, wherein the image sensor comprises a charge-coupled device (CCD).

7. The image sensor of claim 5, wherein the image sensor comprises a CMOS device.

8. The image sensor of claim 1, further comprising a protective layer formed on the circuit elements.

9. The image sensor of claim 5, further comprising a package, wherein the package includes a flange or seal for interface to a vacuum seal.

10. A method of fabricating an image sensor, the method comprising:
    forming an epitaxial layer on a silicon substrate;
    forming a gate layer on the silicon substrate;
    forming a circuit element layer on the gate layer;
    thinning the silicon substrate to generated a thinned substrate, the thinned substrate exposing at least one portion of the epitaxial layer;

doping said at least one exposed portion of the epitaxial layer; and forming a pure boron layer on said at least one exposed portion of the epitaxial layer.

11. The method of claim 10, further comprising forming an anti-reflection coating on the pure boron layer.

12. The method of claim 10, further comprising forming a conductive layer on the pure boron layer.

13. The method of claims 10, further comprising forming a protective layer on the circuit element layer.

14. The method of claim 10, further comprising packing the thinned substrate in a package, wherein the package includes a flange or seal for interface to a vacuum seal.

15. A method of fabricating an image sensor, the method comprising:

forming an epitaxial layer on a silicon substrate;
forming circuit elements on the epitaxial layer;
attaching a handling wafer to the circuit elements;
thinning the silicon substrate to expose a portion of the epitaxial layer;
doping said exposed portion of the epitaxial layer; and
forming a pure boron layer on the exposed portion of the epitaxial layer.

16. The method of claim 15, further comprising forming an anti-reflection coating on the pure boron layer.

17. The method of claim 15, further comprising forming a conductive layer on the pure boron layer.

18. An inspection system comprising:

an illumination source;

optics including an objective lens, the optics configured to direct and focus radiation from the illumination source onto a sample;

a detector configured to receive reflected or scattered light from the sample, wherein the optics are further configured to collect, direct, and focus the reflected or scattered light onto the detector, the detector including one or more image sensors, at least one image sensor including a semiconductor membrane comprising an epitaxial layer and including opposing first and second surfaces, the semiconductor membrane including circuit elements formed on the first surface of the epitaxial layer a dopant formed in the second surface of the epitaxial layer, and a pure boron layer formed on the semiconductor membrane such that a portion of the boron is diffused into the epitaxial layer through the second surface.

* * * * *